(12) United States Patent
Ghosh et al.

(10) Patent No.: US 7,302,348 B2
(45) Date of Patent: Nov. 27, 2007

(54) METHOD AND SYSTEM FOR QUANTIFYING AND REMOVING SPATIAL-INTENSITY TRENDS IN MICROARRAY DATA

(75) Inventors: Jayati Ghosh, San Jose, CA (US); Bill J. Peck, Mountain View, CA (US); Eric M. Leproust, San Jose, CA (US); Charles David Troup, Livermore, CA (US); Glenda Choate Delenstarr, Redwood City, CA (US); Patrick J. Collins, San Francisco, CA (US); John F. Corson, Mountain View, CA (US); Paul K. Wolber, Los Altos, CA (US); Xiangyang Zhou, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 462 days.

(21) Appl. No.: 10/859,868

(22) Filed: Jun. 2, 2004

(65) Prior Publication Data

US 2005/0273268 A1   Dec. 8, 2005

(51) Int. Cl.
*G06F 19/00* (2006.01)
*G06F 15/00* (2006.01)
*G11C 17/00* (2006.01)

(52) U.S. Cl. .............................. 702/19; 700/1; 365/94
(58) Field of Classification Search ..................... None
See application file for complete search history.

(56) References Cited

U.S. PATENT DOCUMENTS

| | | | |
|---|---|---|---|
| 4,707,647 A | 11/1987 | Coldren et al. |
| 5,019,997 A | 5/1991 | Halter |
| 5,086,319 A | 2/1992 | Carolan |
| 5,581,487 A | 12/1996 | Kelly et al. |
| 5,599,695 A | 2/1997 | Pease et al. |
| 5,721,435 A | 2/1998 | Troll |
| 5,744,305 A | 4/1998 | Fodor et al. |
| 5,753,788 A | 5/1998 | Fodor et al. |
| 5,801,970 A | 9/1998 | Rowland et al. |
| 5,812,272 A | 9/1998 | King et al. |
| 5,834,758 A | 11/1998 | Trulson et al. |
| 5,837,475 A | 11/1998 | Dorsel et al. |
| 5,861,242 A | 1/1999 | Chee et al. |
| 5,948,902 A | 9/1999 | Honkanen et al. |
| 6,171,797 B1 | 1/2001 | Perbost |
| 6,180,351 B1 | 1/2001 | Cattell |
| 6,232,072 B1 | 5/2001 | Fisher |
| 6,242,266 B1 | 6/2001 | Schliefer et al. |
| 6,251,685 B1 | 6/2001 | Dorsel et al. |
| 6,258,536 B1 | 7/2001 | Oliner et al. |
| 6,269,322 B1 | 7/2001 | Templeton et al. |
| 6,323,043 B1 | 11/2001 | Caren et al. |
| 6,329,143 B1 | 12/2001 | Stryer et al. |
| 6,344,316 B1 | 2/2002 | Lockhart et al. |
| 6,345,115 B1 | 2/2002 | Ramm et al. |
| 6,349,144 B1 | 2/2002 | Shams |
| 6,355,423 B1 | 3/2002 | Rothberg et al. |
| 6,406,849 B1 | 6/2002 | Dorsel et al. |
| 6,571,005 B1 | 5/2003 | Li et al. |
| 6,674,882 B1 | 1/2004 | Shams |
| 2002/0160369 A1 | 10/2002 | Dorsel et al. |
| 2003/0160183 A1 | 8/2003 | Dorsel et al. |
| 2003/0216870 A1 | 11/2003 | Wolber et al. |
| 2004/0021055 A1 | 2/2004 | Corson et al. |
| 2004/0023224 A1 | 2/2004 | Corson et al. |

FOREIGN PATENT DOCUMENTS

| | | |
|---|---|---|
| EP | 1 162 572 A2 | 12/2001 |
| WO | WO 99/08233 | 2/1999 |
| WO | WO 01/06395 | 1/2001 |
| WO | WO 01/81542 | 11/2001 |

OTHER PUBLICATIONS

Cheung, et al., "Analysis of Gene Microarray Images," 1999, IEEE, pp. 627-632.
Kuklin, et al., "High throughput screening of gene expression signatures," 2000, Genetica 108, pp. 41-46.
Tseng et al., "Issues in cDNA microarray analysis: quality filtering, channel normalization, models of variations and assessment of gene effects," 2001 Oxford University Press, pp. 2549-2557.
Bowtel, Options available -from start to finish- for obtaining expression data by microarray, Nat Genet. Jan. 21, 1999,(1 suppl):25-32.
Yang et al., Normalization for cDNA microarray data: a robust composite method addressing single and multiple slide systematic variation., Nucleic Acids Res. Feb. 15, 2002;30(4):e15.
Bozinov, Unsupervised technique for robust target separation and analysis of DNA microarray spots through adaptive pixel clustering., Bioinformatics. May 2002; 18(5):747-56.
Press, William H., et al. "Numerical Recipes in C, The Art of Scientific Computing," 1987, pp. 248-250 and 558-565.

*Primary Examiner*—John S Brusca

(57) ABSTRACT

A method and system for quantifying and correcting spatial-intensity trends for each channel of a microarray data set having one or more channels. The method and system of one embodiment of the present invention selects a set of features from each channel of the microarray data set. Based on the selected set of features, a surface is used to determine the intensities for all features in each channel of the microarray data set. Spatial-intensity trends within the microarray data set are quantified, based on the surface to the intensities for each channel of the microarray data set. After the surface has been determined, the spatial-intensity trend can be removed from the microarray data set.

22 Claims, 21 Drawing Sheets

METHOD AND SYSTEM FOR QUANTIFYING AND REMOVING SPATIAL-INTENSITY TRENDS IN MICROARRAY DATA

Embodiments of the present invention are related to microarrays, and, in particular, to a method and system for quantifying and correcting for trends present in feature signal intensities of microarray data.

BACKGROUND OF THE INVENTION

The present invention is related to microarrays. In order to facilitate discussion of the present invention, a general background for particular types of microarrays is provided below. In the following discussion, the terms "microarray," "molecular array," and "array" are used interchangeably. The terms "microarray" and "molecular array" are well known and well understood in the scientific community. As discussed below, a microarray is a precisely manufactured tool which may be used in research, diagnostic testing, or various other analytical techniques to analyze complex solutions of any type of molecule that can be optically or radiometrically detected and that can bind with high specificity to complementary molecules synthesized within, or bound to, discrete features on the surface of a microarray. Because microarrays are widely used for analysis of nucleic acid samples, the following background information on microarrays is introduced in the context of analysis of nucleic acid solutions following a brief background of nucleic acid chemistry.

Deoxyribonucleic acid ("DNA") and ribonucleic acid ("RNA") are linear polymers, each synthesized from four different types of subunit molecules. FIG. 1 illustrates a short DNA polymer 100, called an oligomer, composed of the following subunits: (1) deoxy-adenosine 102; (2) deoxy-thymidine 104; (3) deoxy-cytosine 106; and (4) deoxy-guanosine 108. Phosphorylated subunits of DNA and RNA molecules, called "nucleotides," are linked together through phosphodiester bonds 110-115 to form DNA and RNA polymers. A linear DNA molecule, such as the oligomer shown in FIG. 1, has a 5' end 118 and a 3' end 120. A DNA polymer can be chemically characterized by writing, in sequence from the 5' end to the 3' end, the single letter abbreviations A, T, C, and G for the nucleotide subunits that together compose the DNA polymer. For example, the oligomer 100 shown in FIG. 1 can be chemically represented as "ATCG."

The DNA polymers that contain the organization information for living organisms occur in the nuclei of cells in pairs, forming double-stranded DNA helices. One polymer of the pair is laid out in a 5' to 3' direction, and the other polymer of the pair is laid out in a 3' to 5' direction, or, in other words, the two strands are anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. FIGS. 2A-B illustrates the hydrogen bonding between the purine and pyrimidine bases of two anti-parallel DNA strands. AT and GC base pairs, illustrated in FIGS. 2A-B, are known as Watson-Crick ("WC") base pairs. Two DNA strands linked together by hydrogen bonds forms the familiar helix structure of a double-stranded DNA helix. FIG. 3 illustrates a short section of a DNA double helix 300 comprising a first strand 302 and a second, anti-parallel strand 304.

Double-stranded DNA may be denatured, or converted into single stranded DNA, by changing the ionic strength of the solution containing the double-stranded DNA or by raising the temperature of the solution. Single-stranded DNA polymers may be renatured, or converted back into DNA duplexes, by reversing the denaturing conditions, for example by lowering the temperature of the solution containing complementary single-stranded DNA polymers. During renaturing or hybridization, complementary bases of anti-parallel DNA strands form WC base pairs in a cooperative fashion, leading to reannealing of the DNA duplex.

FIGS. 4-7 illustrate the principle of the microarray-based hybridization assay. A microarray (402 in FIG. 4) comprises a substrate upon which a regular pattern of features is prepared by various manufacturing processes. The microarray 402 in FIG. 4, and in subsequent FIGS. 5-7, has a grid-like 2-dimensional pattern of square features, such as feature 404 shown in the upper left-hand corner of the microarray. Each feature of the microarray contains a large number of identical oligonucleotides covalently bound to the surface of the feature. These bound oligonucleotides are known as probes. In general, chemically distinct probes are bound to the different features of a microarray, so that each feature corresponds to a particular nucleotide sequence.

Once a microarray has been prepared, the microarray may be exposed to a sample solution of target DNA or RNA molecules (410-413 in FIG. 4) labeled with fluorophores, chemiluminescent compounds, or radioactive atoms 415-418. Labeled target DNA or RNA hybridizes through base pairing interactions to the complementary probe DNA, synthesized on the surface of the microarray. FIG. 5 shows a number of such target molecules 502-504 hybridized to complementary probes 505-507, which are in turn bound to the surface of the microarray 402. Targets, such as labeled DNA molecules 508 and 509, that do not contain nucleotide sequences complementary to any of the probes bound to the microarray surface do not hybridize to generate stable duplexes and, as a result, tend to remain in solution. The sample solution is then rinsed from the surface of the microarray, washing away any unbound-labeled DNA molecules. In other embodiments, unlabeled target sample is allowed to hybridize with the microarray first. Typically, such a target sample has been modified with a chemical moiety that will react with a second chemical moiety in subsequent steps. Then, either before or after a wash step, a solution containing the second chemical moiety bound to a label is reacted with the target on the microarray. After washing, the microarray is ready for analysis. Biotin and avidin represent an example of a pair of chemical moieties that can be utilized for such steps.

Finally, as shown in FIG. 6, the bound labeled DNA molecules are detected via optical or radiometric instrumental detection. Optical detection involves exciting labels of bound labeled DNA molecules with electromagnetic radiation of appropriate frequency and detecting fluorescent emissions from the labels, or detecting light emitted from chemiluminescent labels. When radioisotope labels are employed, radiometric detection can be used to detect the signal emitted from the hybridized features. Additional types of signals are also possible, including electrical signals generated by electrical properties of bound target molecules, magnetic properties of bound target molecules, and other such physical properties of bound target molecules that can produce a detectable signal. Optical, radiometric, or other types of instrumental detection produce an analog or digital representation of the microarray as shown in FIG. 7, with features to which labeled target molecules are hybridized similar to 702 optically or digitally differentiated from those features to which no labeled DNA molecules are bound. Features displaying positive signals in the analog or digital representation indicate the presence of DNA molecules with complementary nucleotide sequences in the original sample solution. Moreover, the signal intensity produced by a feature is generally related to the amount of labeled DNA bound to the feature, in turn related to the concentration, in the sample to which the microarray was exposed, of labeled DNA complementary to the oligonucleotide within the feature.

One, two, or more than two data subsets within a data set can be obtained from a single microarray by scanning or reading the microarray for one, two or more than two types of signals. Two or more data subsets can also be obtained by combining data from two different arrays. When optical detection is used to detect fluorescent or chemiluminescent emission from chromophore labels, a first set of signals, or data subset, may be generated by reading the microarray at a first optical wavelength, a second set of signals, or data subset, may be generated by reading the microarray at a second optical wavelength, and additional sets of signals may be generated by detection or reading the microarray at additional optical wavelengths. Different signals may be obtained from a microarray by radiometric detection of radioactive emissions at one, two, or more than two different energy levels. Target molecules may be labeled with either a first chromophore that emits light at a first wavelength, or a second chromophore that emits light at a second wavelength. Following hybridization, the microarray can be read at the first wavelength to detect target molecules, labeled with the first chromophore, hybridized to features of the microarray, and can then be read at the second wavelength to detect target molecules, labeled with the second chromophore, hybridized to the features of the microarray. In one common microarray system, the first chromophore emits light at a near infrared wavelength, and the second chromophore emits light at a yellow visible-light wavelength, although these two chromophores, and corresponding signals, are referred to as "red" and "green." The data set obtained from reading the microarray at the red wavelength is referred to as the "red signal," and the data set obtained from reading the microarray at the green wavelength is referred to as the "green signal." While it is common to use one or two different chromophores, it is possible to use one, three, four, or more than four different chromophores and to read a microarray at one, three, four, or more than four wavelengths to produce one, three, four, or more than four data sets. With the use of quantum-dot dye particles, the emission is tunable by suitable engineering of the quantum-dot dye particles, and a fairly large set of such quantum-dot dye particles can be excited with a single-color, single-laser-based excitation.

Sources of background signal can inflate the signal intensities associated with certain of the features of the microarray. The background signal of a microarray may contribute systematic feature-position-related background intensity to the measured intensity data read from the microarray and may cause inaccurate determination of gene expression levels during analysis. Therefore, experimentalist, designers, and manufacturers of microarrays and microarray data processing systems have recognized a need for a reliable and efficient method and system for quantifying and removing any systematic feature-position-related background intensities within a microarray data set.

SUMMARY OF THE INVENTIOIN

Various embodiments of the present invention detect and remove systematic background signal from a microarray data set. One embodiment of the present invention provides a method and system for quantifying and correcting spatial-intensity trends within a microarray data set having one or more channels. The method and system of one embodiment of the present invention selects a set of features from each channel of a microarray data set. Based on the selected set or sets of features, a surface is constructed and used to determine the intensities of all features in each channel of the microarray data set. Spatial-intensity trends within the microarray data set are quantified, based on the constructed surface. Quantified spatial-intensity trends can then be removed from the microarray data set by subtracting the constructed surface value for each corresponding feature intensity.

DETAILED DESCRIPTION OF EMBODIMENTS OF THE INVENTION

Figure 1:
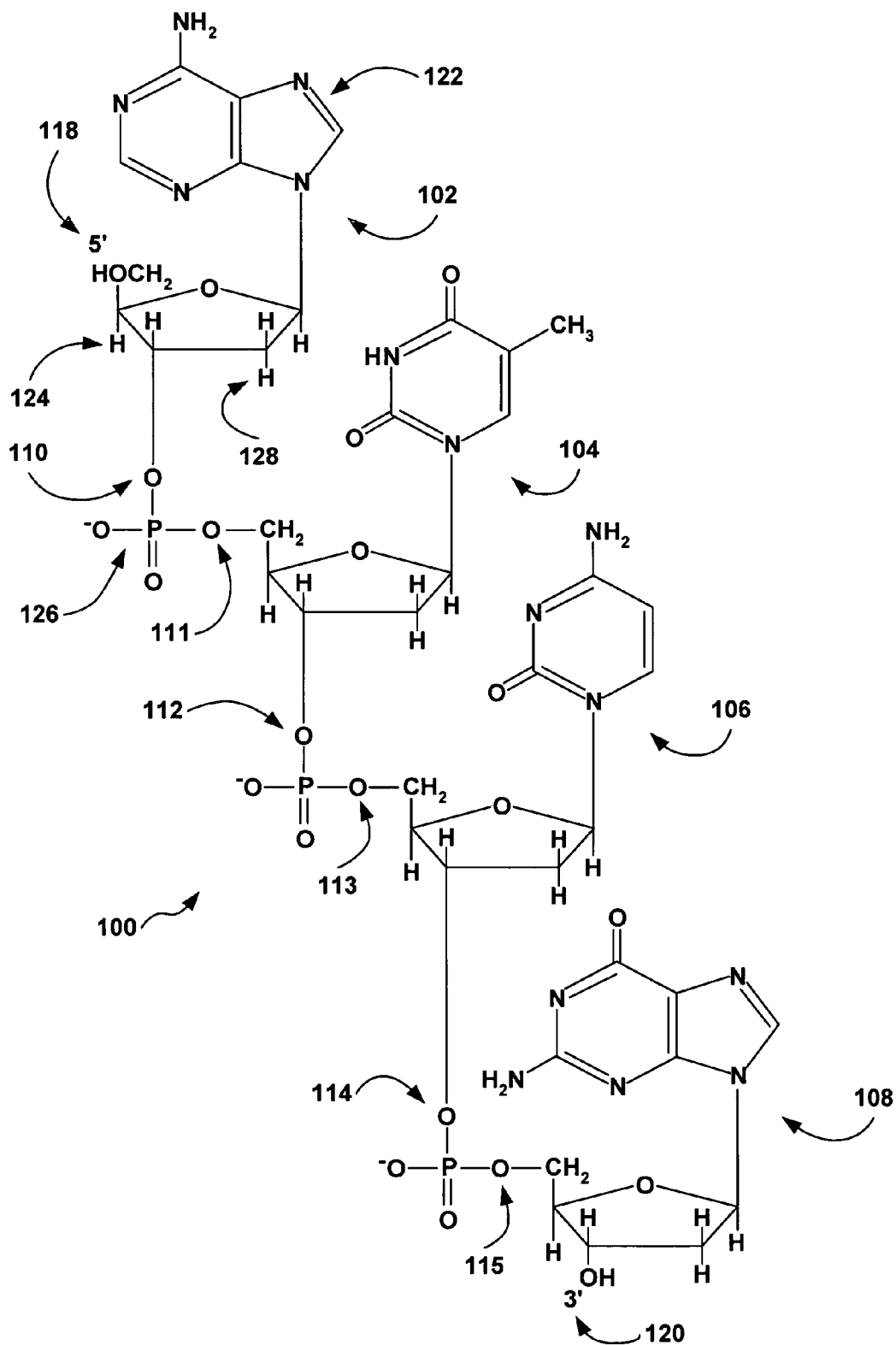
FIG. 1 illustrates a short DNA polymer.
Figure 2A:
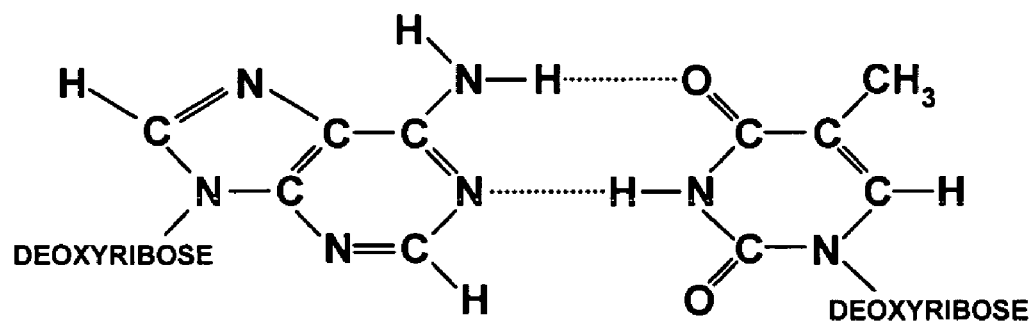
FIGS. 2A-B illustrate the hydrogen bonding between the purine and pyrimidine bases of two anti-parallel DNA strands.
Figure 2B:
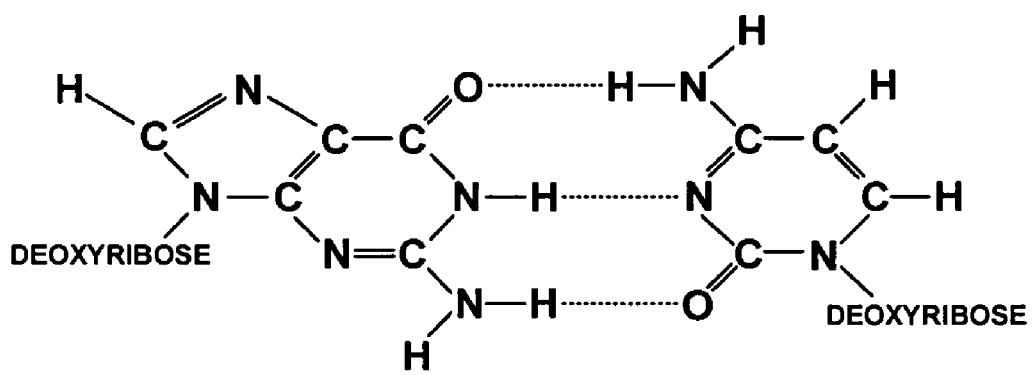
Figure 3:
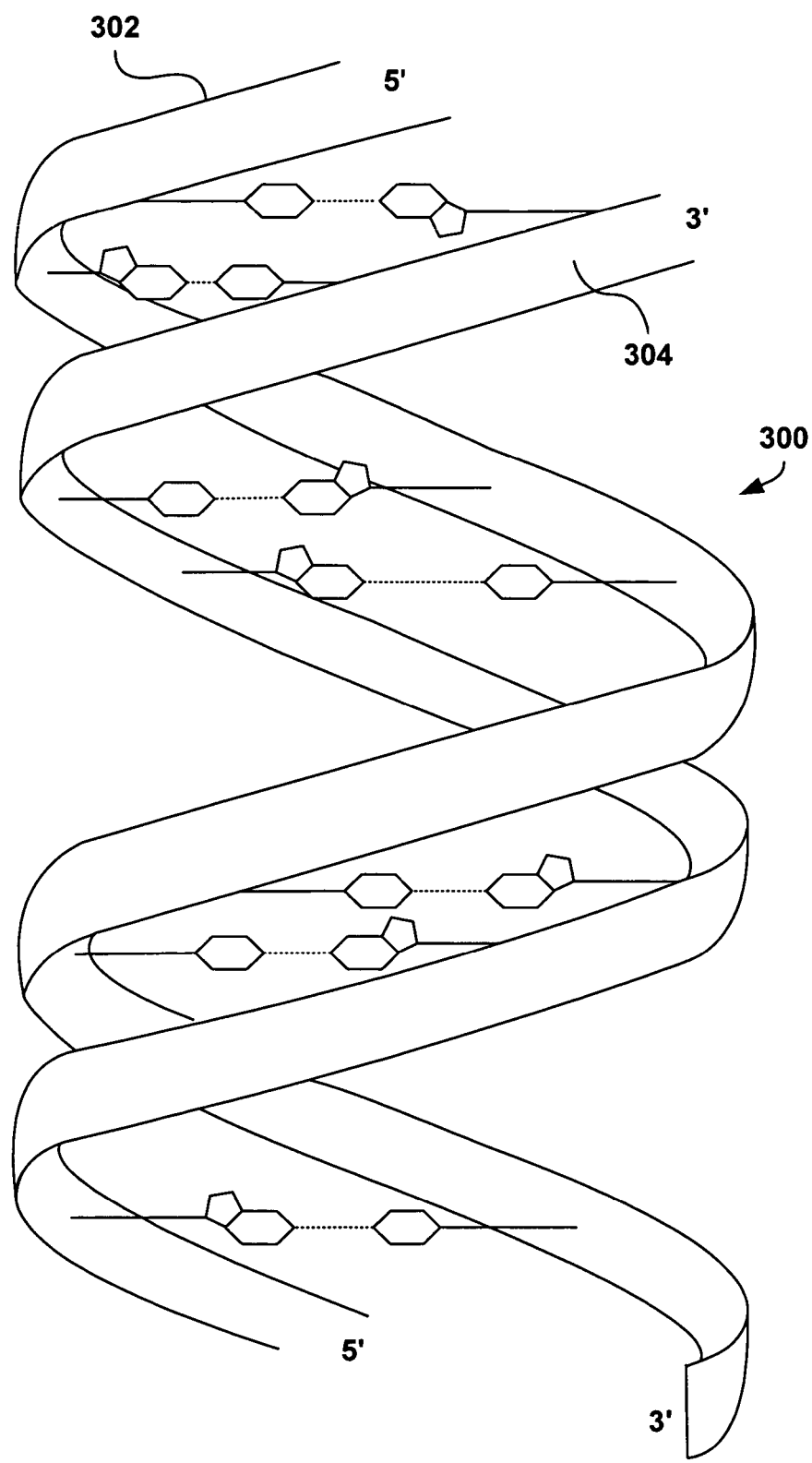
FIG. 3 illustrates a short section of a DNA double helix comprising a first strand and a second, anti-parallel strand.
Figure 4:
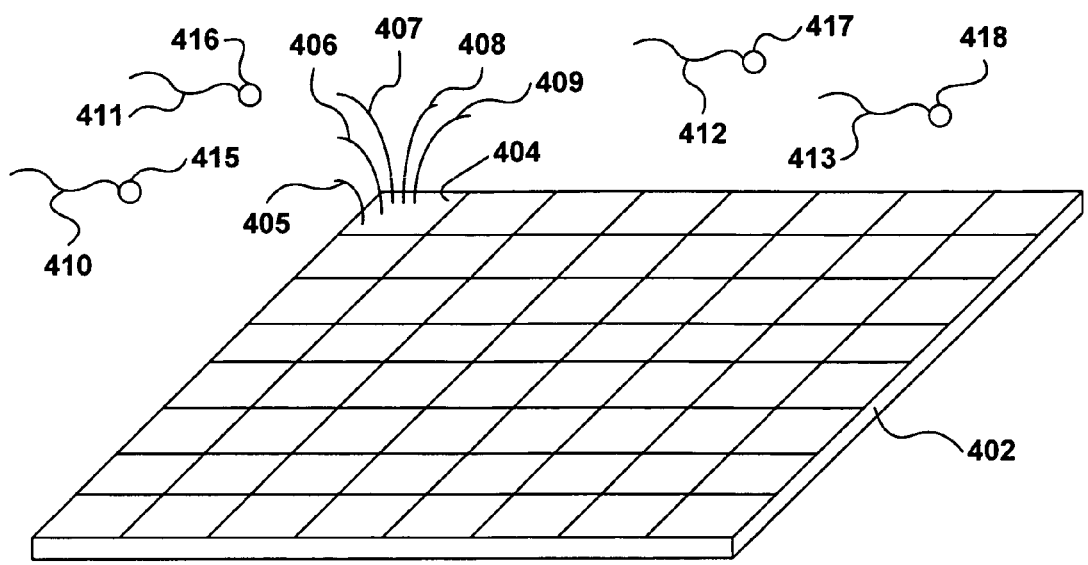
FIG. 4 illustrates a grid-like, two-dimensional pattern of square features.
Figure 5:
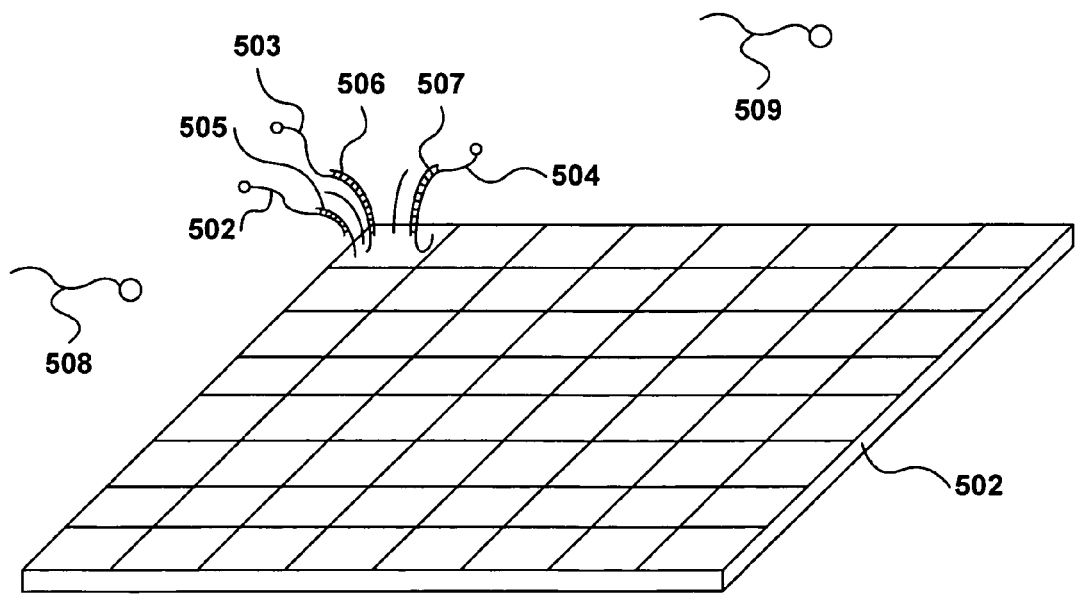
FIG. 5 shows a number of target molecules hybridized to complementary probes, which are in turn bound to the surface of the microarray.
Figure 6:
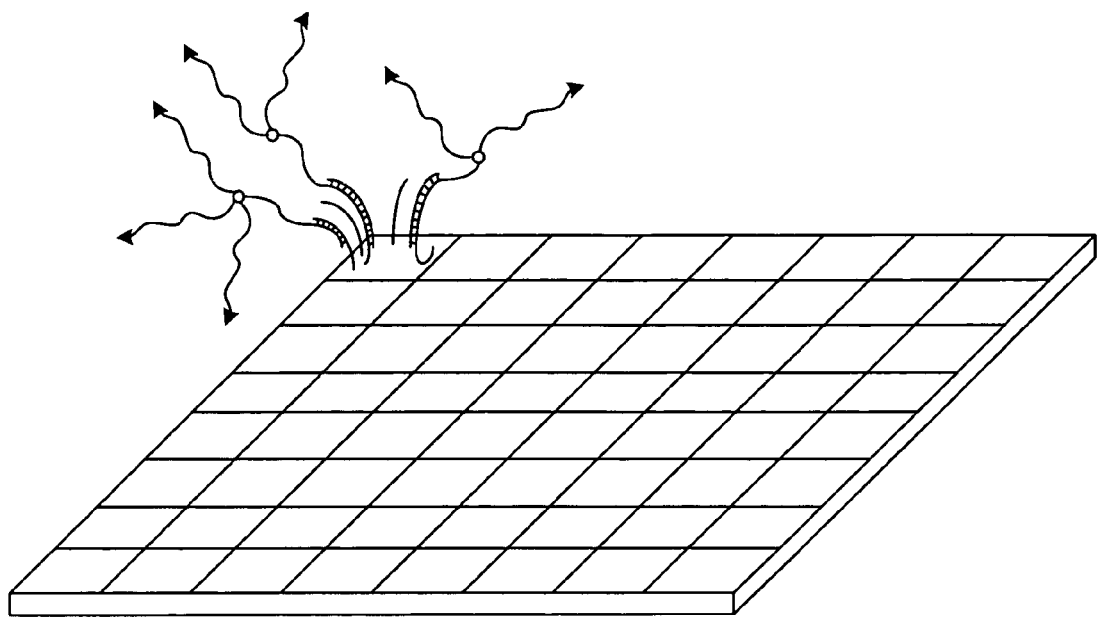
FIG. 6 illustrates the bound labeled DNA molecules detected via optical or radiometric scanning.
Figure 7:
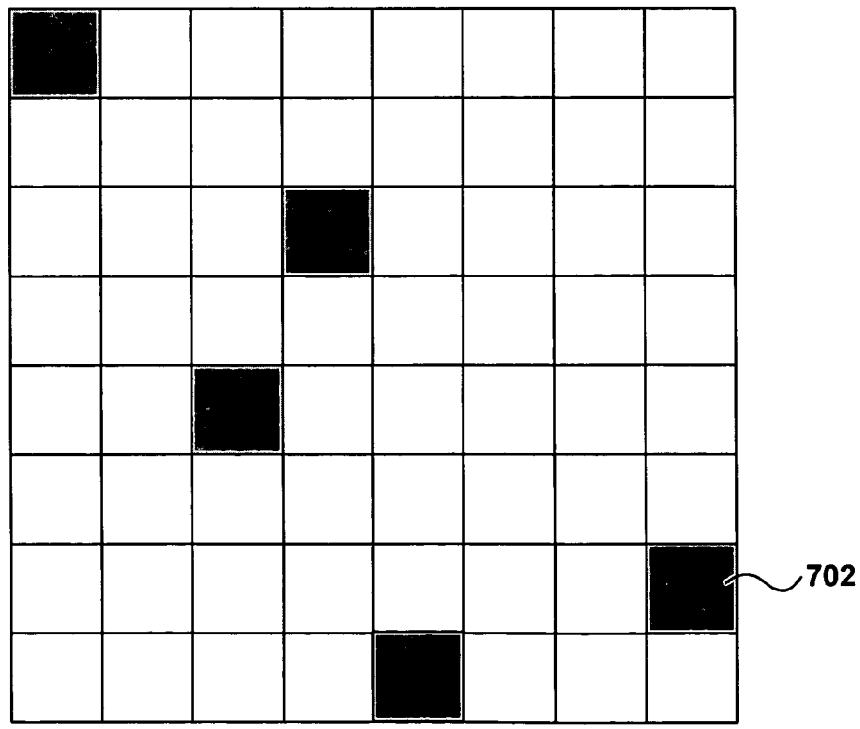
FIG. 7 illustrates optical, radiometric, or other types of scanning produced by an analog or digital representation of the microarray.

Embodiments of the present invention are directed toward a method for quantifying and correcting spatial-intensity trends in microarray data. The following discussion includes two subsections, a first subsection including additional information about molecular arrays, and a second subsection describing embodiments of the present invention with reference to FIGS. 11-20.

Additional Information About Microarrays

A microarray may include any one-, two- or three-dimensional arrangement of addressable regions, or features, each bearing a particular chemical moiety or moieties, such as biopolymers, associated with that region. Any given microarray substrate may carry one, two, or four or more microarrays disposed on a front surface of the substrate. Depending upon the use, any or all of the microarrays may be the same or different from one another and each may contain multiple spots or features. A typical microarray may contain more than ten, more than one hundred, more than one thousand, more ten thousand features, or even more than one hundred thousand features, in an area of less than 20 cm$^2$ or even less than 10 cm$^2$. For example, square features may have widths, or round feature may have diameters, in the range from a 10 μm to 1.0 cm. In other embodiments each feature may have a width or diameter in the range of 1.0 μm to 1.0 mm, usually 5.0 μm to 500 μm, and more usually 10 μm to 200 μm. Features other than round or square may have area ranges equivalent to that of circular features with the foregoing diameter ranges. At least some, or all, of the features may be of different compositions (for example, when any repeats of each feature composition are excluded the remaining features may account for at least 5%, 10%, or 20% of the total number of features). Inter-feature areas are typically, but not necessarily, present. Inter-feature areas generally do not carry probe molecules. Such inter-feature areas typically are present where the microarrays are formed by processes involving drop deposition of reagents, but may not be present when, for example, photolithographic microarray fabrication processes are used. When present, interfeature areas can be of various sizes and configurations.

Each microarray may cover an area of less than 100 cm$^2$, or even less than 50 cm$^2$, 10 cm$^2$ or 1 cm$^2$. In many embodiments, the substrate carrying the one or more microarrays will be shaped generally as a rectangular solid having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. Other shapes are possible, as well. With microarrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, a substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Microarrays can be fabricated using drop deposition from pulsejets of either polynucleotide precursor units (such as monomers) in the case of in situ fabrication, or the previously obtained polynucleotide. Such methods are described in detail in, for example, U.S. Pat. No. 6,242,266, U.S. Pat. No. 6,232,072, U.S. Pat. No. 6,180,351, U.S. Pat No. 6,171,797, U.S. Pat. No. 6,323,043, U.S. patent application Ser. No. 09/302,898 filed Apr. 30, 1999 by Caren et al., and the references cited therein. Other drop deposition methods can be used for fabrication, as previously described herein. Also, instead of drop deposition methods, photolithographic microarray fabrication methods may be used. Interfeature areas need not be present particularly when the microarrays are made by photolithographic methods as described in those patents.

A microarray is typically exposed to a sample including labeled target molecules, or, as mentioned above, to a sample including unlabeled target molecules followed by exposure to labeled molecules that bind to unlabeled target molecules bound to the microarray, and the microarray is then read. Reading of the microarray may be accomplished by illuminating the microarray and reading the location and intensity of resulting fluorescence at multiple regions on each feature of the microarray. For example, a scanner may be used for this purpose, which is similar to the AGILENT MICROARRAY SCANNER manufactured by Agilent Technologies, Palo Alto, Calif. Other suitable apparatus and methods are described in published U.S. patent applications 20030160183A1, 20020160369A1, 20040023224A1, and 20040021055A, as well as U.S. Pat. No. 6,406,849. However, microarrays may be read by any other method or apparatus than the foregoing, with other reading methods including other optical techniques, such as. detecting chemiluminescent or electroluminescent labels, or electrical techniques, for where each feature is provided with an electrode to detect hybridization at that feature in a manner disclosed in U.S. Pat. No. 6,251,685, and elsewhere.

A result obtained from reading a microarray, followed by application of a method of the present invention, may be used in that form or may be further processed to generate a result such as that obtained by forming conclusions based on the pattern read from the microarray, such as whether or not a particular target sequence may have been present in the sample, or whether or not a pattern indicates a particular condition of an organism from which the sample came. A result of the reading, whether further processed or not, may be forwarded, such as by communication, to a remote location if desired, and received there for further use, such as for further processing. When one item is indicated as being remote from another, this is referenced that the two items are at least in different buildings, and may be at least one mile, ten miles, or at least one hundred miles apart. Communicating information references transmitting the data representing that information as electrical signals over a suitable communication channel, for example, over a private or public network. Forwarding an item refers to any means of getting the item from one location to the next, whether by physically tran-sporting that item or, in the case of data, physically transporting a medium carrying the data or communicating the data.

As pointed out above, microarray-based assays can involve other types of biopolymers, synthetic polymers, and other types of chemical entities. A biopolymer is a polymer of one or more types of repeating units. Biopolymers are typically found in biological systems and particularly include polysaccharides, peptides, and polynucleotides, as well as their analogs such as those compounds composed of, or containing, amino acid analogs or non-amino-acid groups, or nucleotide analogs or non-nucleotide groups. This includes polynucleotides in which the conventional backbone has been replaced with a non-naturally occurring or synthetic backbone, and nucleic acids, or synthetic or naturally occurring nucleic-acid analogs, in which one or more of the conventional bases has been replaced with a natural or synthetic group capable of participating in Watson-Crick-type hydrogen bonding interactions. Polynucleotides include single or multiple-stranded configurations, where one or more of the strands may or may not be completely aligned with another. For example, a biopolymer includes DNA, RNA, oligonucleotides, and PNA and other polynucleotides as described in U.S. Pat. No. 5,948,902 and references cited therein, regardless of the source. An oligonucleotide is a nucleotide multimer of about 10 to 100 nucleotides in length, while a polynucleotide includes a nucleotide multimer having any number of nucleotides.

As an example of a non-nucleic-acid-based microarray, protein antibodies may be attached to features of the microarray that would bind to soluble labeled antigens in a sample solution. Many other types of chemical assays may be facilitated by microarray technologies. For example, polysaccharides, glycoproteins, synthetic copolymers, including block copolymers, biopolymer-like polymers with synthetic or derivitized monomers or monomer linkages, and many other types of chemical or biochemical entities may serve as probe and target molecules for microarray-based analysis. A fundamental principle upon which microarrays are based is that of specific recognition, by probe molecules affixed to the microarray, of target molecules, whether by sequence-mediated binding affinities, binding affinities based on conformational or topological properties of probe and target molecules, or binding affinities based on spatial distribution of electrical charge on the surfaces of target and probe molecules.

Scanning of a microarray by an optical scanning device or radiometric scanning device generally produces an image comprising a rectilinear grid of pixels, with each pixel having a corresponding signal intensity. These signal intensities are processed by a microarray-data-processing program that analyzes data scanned from an microarray to produce experimental or diagnostic results which are stored in a computer-readable medium, transferred to an intercommunicating entity via electronic signals, printed in a human-readable format, or otherwise made available for further use. Microarray experiments can indicate precise gene-expression responses of organisms to drugs, other chemical and biological substances, environmental factors, and other effects. Microarray experiments can also be used to diagnose disease, for gene sequencing, and for analytical chemistry. Processing of microarray data can produce detailed chemical and biological analyses, disease diagnoses, and other information that can be stored in a computer-readable medium, transferred to an intercommunicating entity via electronic signals, printed in a human-readable format, or otherwise made available for further use.

Embodiments of the Present Invention

In general, the intensity associated with a feature of a microarray is the sum of: (1) a first signal-intensity component produced by bound target molecule labels; and (2) a second signal-intensity component, referred to as the "background," which may be the product of a wide variety of background-intensity-producing sources, including noise produced by electronic and optical components of a microarray scanner, general non-specific reflection of light from the surface of the microarray during scanning, or, in the case of radio-labeled target molecules, natural sources of background radiation, and various defects and contaminants on, and damage associated with, the surface of the microarray. Background may also me the result of a contaminant bound to the probes, or to an underlying silane layer, or impurities in glass underlying the silane layer. Background signal may also be due to varying amounts of non-specific binding of labeled target.

The background may also contain signal intensities resulting from signals emitted by probes bound to a feature, which in turn, may be the result of weak intrinsic fluorescent properties of probe molecules and a stronger contribution induced by radiation used to stimulate emission from hybridized target molecule labels. The signals emitted by bound probe nucleotides may be sequence dependent. For example, in the case of the signal strengths produced by the four DNA nucleotide bases background signal emitted by individual nucleotides vary from a relatively weak signal produced by deoxy-adenosine, to intermediate signal strengths produced by deoxy-thymidine and deoxy-guanosine, in that order of respective strengths, to a relatively strongest signal-intensity produced by deoxy-cytosine. Therefore, oligonucleotide probes with a high proportion of A's produce smaller second signal intensity components, while oligonucleotide probes with a high proportion of C's produce larger second signal intensity component. The strength of the induced signal emitted by probes may also be proportional to the nucleotide sequence mass.

Figure 8:
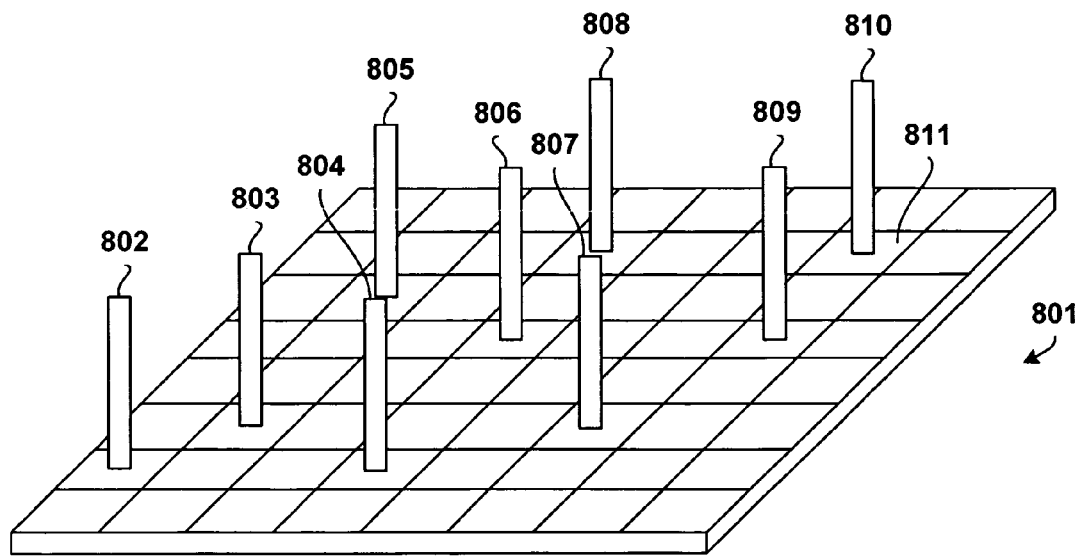
FIG. 8 illustrates an ideal, hypothetical microarray having no spatial-intensity trend.
Figure 9:
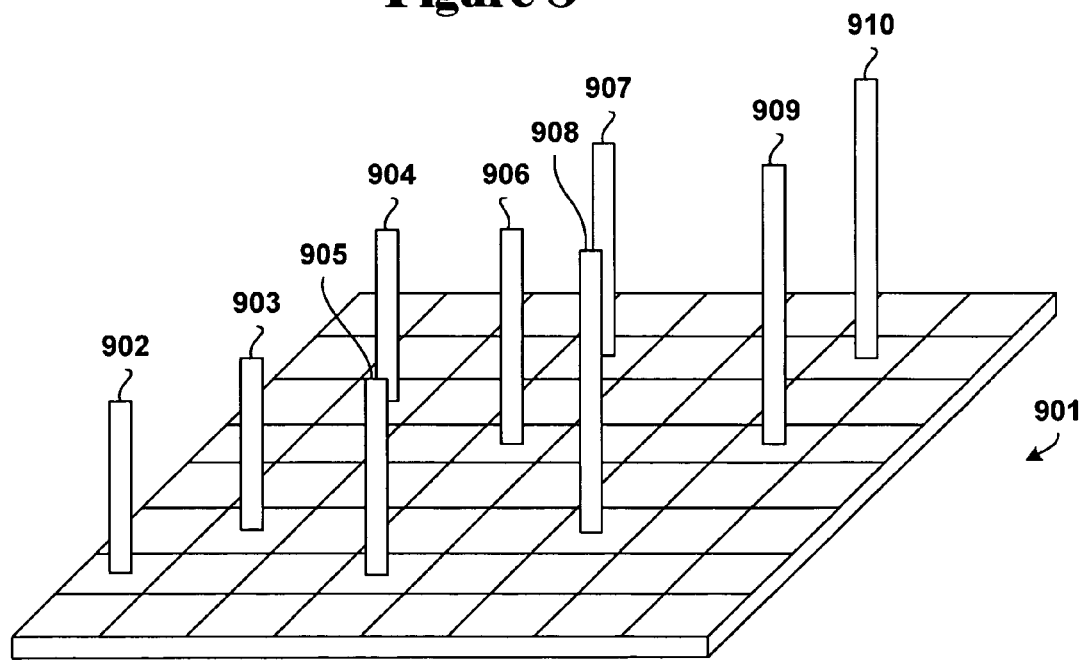
FIG. 9 illustrates a hypothetical microarray having a spatial-intensity trend.

Ideally, randomly distributed microarray features having bound probes with identical nucleotide sequences should emit substantially identical signal intensity when measured by a microarray reader. A variation in signal or background intensities across a microarray surface is referred to as a "spatial-intensity trend." Features having signal-intensities within about 2 to 3 standard deviations of the negative control features, referred to as the "lowest-signal-intensity features," can be used to identify the presence of a spatial-intensity trend in the background. FIG. 8 illustrates an ideal, hypothetical microarray having no apparent spatial-intensity trend. In FIG. 8, the red-channel, lowest-signal-intensity features of the microarray 801 are identified by bars 802-810 extending above the microarray surface. The height of each bar represents the signal-intensity strength emitted by the corresponding feature below. For example, the height of bar 810 above feature 811 represents the red-signal-intensity strength emitted by feature 811. Because the bars 802-811 are all approximately the same height, there appears to be no spatial-intensity trend present for the red channel of the microarray 801. By contrast, FIG. 9 illustrates a hypothetical microarray having an apparent spatial-intensity trend. In FIG. 9, the red-channel, lowest-signal-intensity features of microarray 901 are identified by bars 902-910. The spatial-intensity trend is observed by the increase in the height of bars from left to right. For example, bars 902-904 are shorter than the bars 905-907, which, in turn, are shorter than bars 908-910.

Figure 10A:
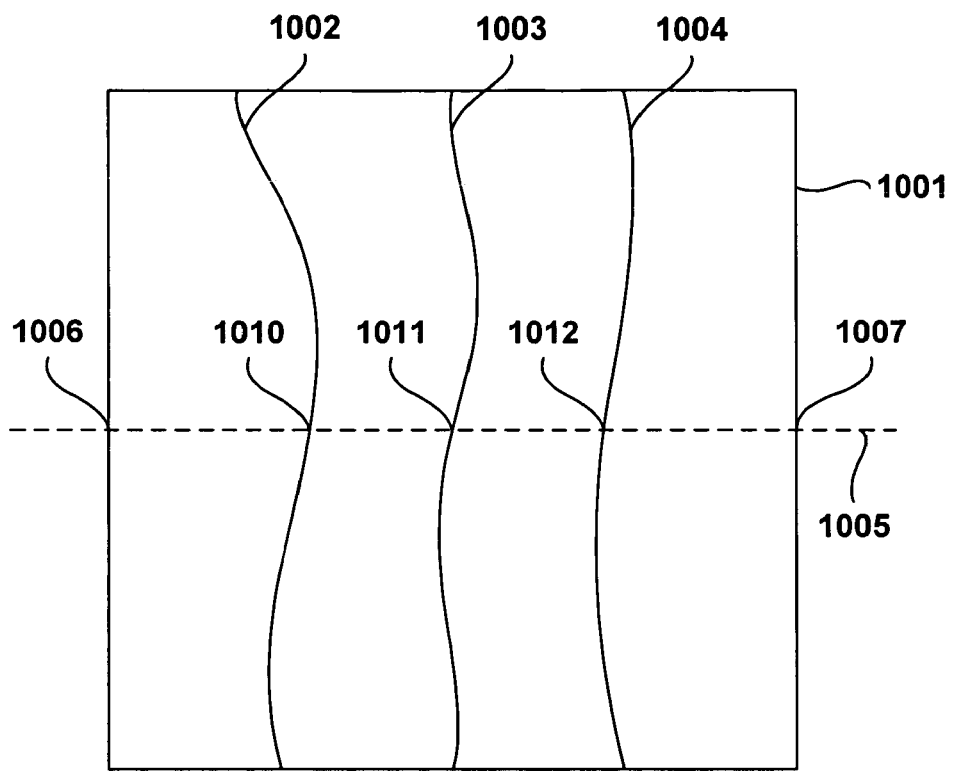
FIGS. 10A-B show a contour plot of a spatial-intensity trend for a hypothetical microarray and a path through the contour plot.
Figure 10B:
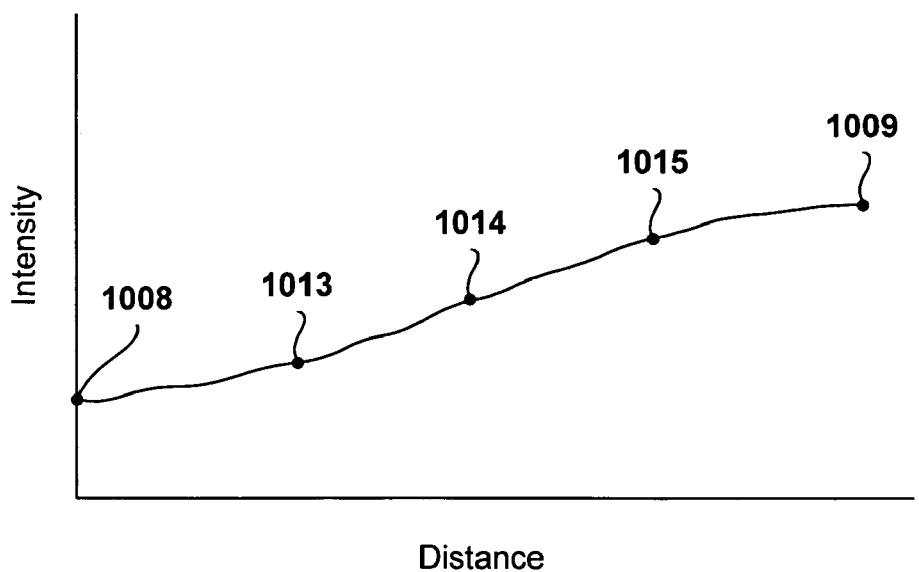

FIGS. 10A-B illustrates a spatial-intensity trend using a contour plot of the lowest-signal-intensity features for one channel of a microarray 1001. A contour line indicates a set of features all with nearly equal intensities, just as a contour line on topographic map indicates terrain at a particular elevation. In FIG. 10A, contour lines 1002-1004 identify lowest-signal-intensity features having intensity values, increasing from left to right. FIG. 10B shows a graph of feature intensity values versus position along a horizontal line roughly bisecting the contour plot shown in FIG. 10A. The plot shown in FIG. 10B may be obtained by plotting the intensity values associated with features along bisecting line 1005 in FIG. 10A. In FIG. 10B, points 1008 and 1009 correspond to the points 1006 and 1007 in FIG. 10A, respectively. FIG. 10B is essentially a vertical cross-section, along line 1005, of the intensity map shown in FIG. 10A. The increasing signal trend represented by contour lines in FIG. 10A is readily observed as a slope in intensity values rising towards the right-hand side of the plot in FIG. 10B. Note that FIGS. 8-10 relate to a spatial intensity trends observed in lowest-signal intensity features, which tend to be features with no specifically bound target molecule labels. However, the spatial-intensity trend may also be observed in the highest signal intensity features. For example, spatial-intensity trends due to artifacts of hybridization or wash tend to show up in the highest-signal intensity features. A spatial-intensity trend in the brighter features is often proportional to the intensity of the signal. In other words, the spatial-intensity trend is a multiplier to the signal intensity. For example, a feature having a signal intensity of 1000 may be increased to 1100, while a feature having a signal intensity of 10,000 may be increased to 11,000.

Figure 11:
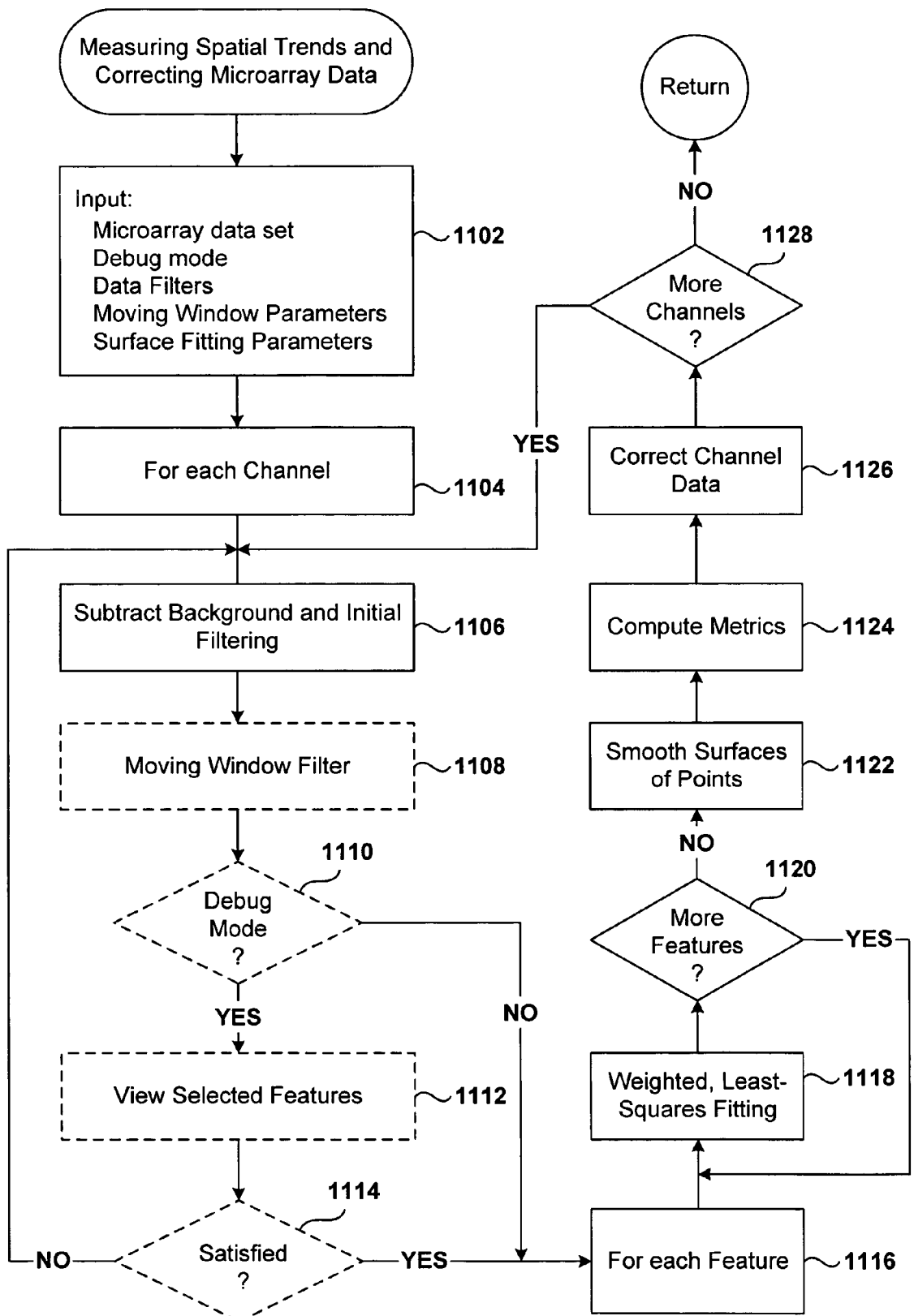
FIG. 11 is a control-flow diagram that describes one of many possible embodiments of the present invention.

One of many possible embodiments of the present invention is directed to a method for detecting, quantifying, and correcting spatial-intensity trends in microarray data. FIG. 11 is a control-flow diagram that describes one of many possible embodiments of the present invention. The method diagrammed in FIG. 11 is discussed below with reference both to FIG. 11 and to subsequence figures that provide greater detail for many of the steps show in FIG. 11.

In an initial step 1102, a user interface is employed to receive a multi-channel microarray data set, determine whether debugging is employed, and to receive data filters, moving window parameters, such as size, increment, and fraction of features selected, and best-fit surface parameters. The data set may comprise two data subsets corresponding to two different channels of one microarray, or may comprise one data subset corresponding to signals obtained from one channel of a microarray. The feature intensities of the data set can be provided in many forms, including raw intensities, background-subtracted intensities, and signal-intensity ratios for features generated form signals obtained from two different channels.

Figure 12:
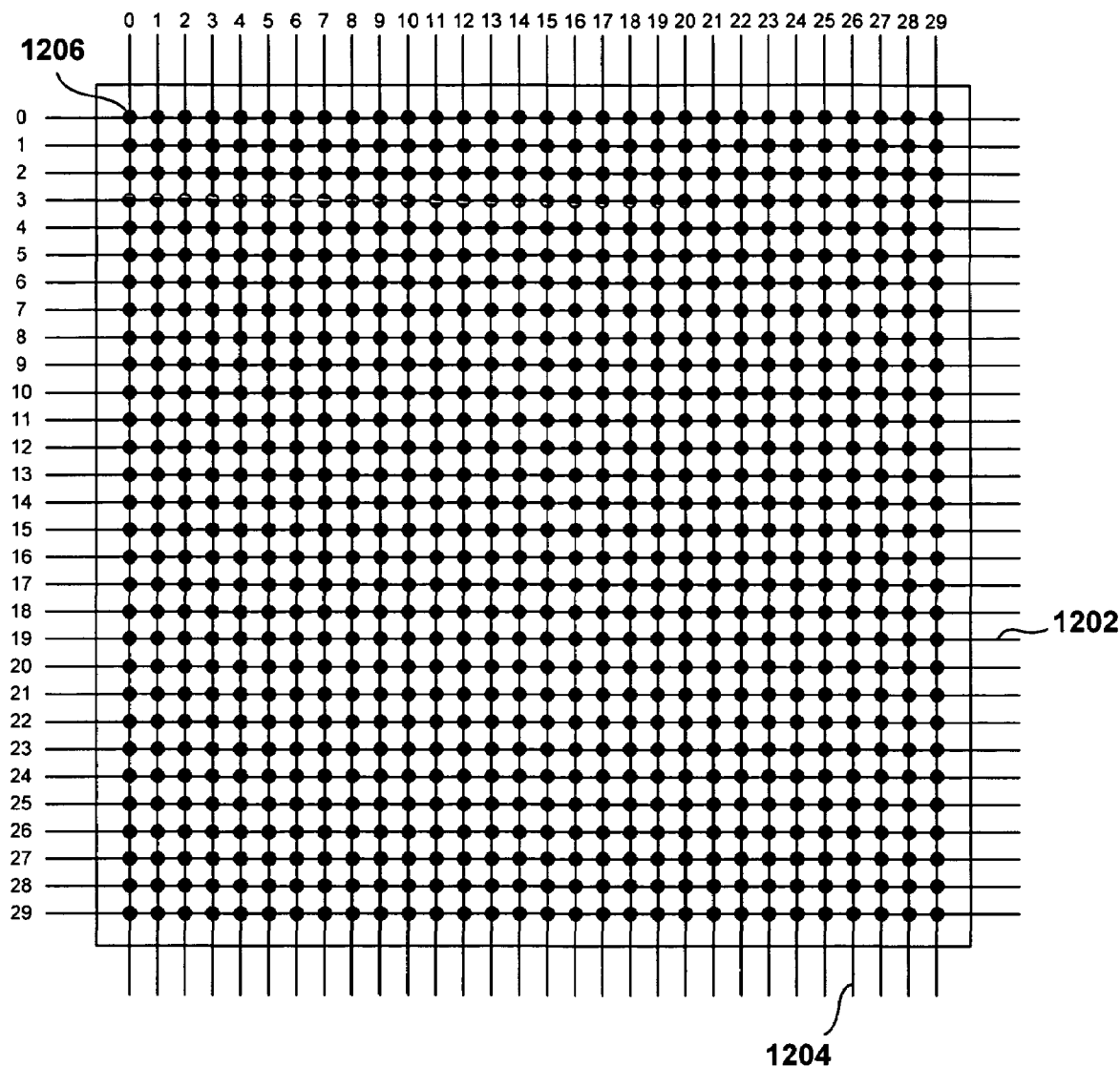
FIG. 12 illustrates indexing features of a microarray.

The microarray data is indexed to provide location coordinates for each feature. FIG. 12 illustrates indexing of features of a microarray. A set of horizontal and vertical grid lines, such as horizontal line 1202 and vertical line 1204, are arranged so that the intersections of horizontal and vertical grid lines correspond to centers of features. The imaginary grid lines establish a two-dimensional index grid for indexing the microarray features. The entire set of microarray features is denoted by $\{(x,y),I,c\}$, where $(x, y)$ corresponds to the feature coordinates of a feature having signal intensity $I$, and a channel index $c$. The total number of microarray features is denoted by L. For example, the coordinates for feature 1206 are (0, 0). For alternative arrangements of features, such as offsetting alternating columns of features, a different indexing system may be used. For example, feature location in odd-indexed rows having a particular column index may be understood to be physically offset horizontally from feature locations having the same column index in even-indexed rows. Such horizontal offsets occur, for example, in hexagonal, closest-packed microarrays of features.

Next, in step 1104, the outer for-loop executes steps 1106-1120 separately for each channel of the multi-channel, microarray data set. In step 1106, the background of the microarray features is subtracted according to a method described in Agilent U.S. patent application Ser. No. 10/153,345, which is incorporated by reference, and Agilent U.S. patent application entitled "Method and System for Computing and Applying a User-Defined, Global, Multi-Channel Background Correction to a Feature-Based Data Set Obtained from Reading a Molecular Array," filed the same day as the present invention, which is incorporated by reference. In addition, the features are filtered by removing features having signal intensities above a threshold value and irregularly shaped features. Note that the term "filtered" does not actually mean feature data is removed from the microarray data set. Instead, filtering involves identifying lowest-signal-intensity features from which to quantify any spatial-intensity trend that may be present.

Filters employed in step 1106 include, but are not limited to: (1) a filter that removes positive control features from consideration because these features typically emit strong signal intensities; (2) a filter that removes non-control features with intensity levels above a threshold saturation level; (3) a filter that removes features having a non-uniform intensity distribution; (4) a filter that removes all features except negative-control features; (5) a filter that leaves only features that are brighter than the mean or median signal on the microarray; (6) a filter that removes all but the brightest features, such as the bightest 1%, 5%, 10%, or 50% or more; and (7) a filter that retains only positive control features.

A filter designed to remove from consideration non-control saturated features with intensity levels above a threshold saturation level is described below. An image of a microarray may consist of a 2-dimensional array of pixel-intensity values, commonly stored in 16-bit words, and therefore ranging from 0 to 65535. A pixel having an intensity value of 65535 is considered to be saturated, because all measured intensity values equal to or greater than 65335 are encoded as the maximum value 65535. When more than a threshold percentage of the pixels within an area corresponding to a feature are saturated, the feature is considered to be saturated. In other words, the true intensity of the feature is not reflected in the intensity value integrated over the pixels within the feature area. For example, a saturation-level threshold of 5% results in the removal of features having more than 5% saturated pixels.

Figure 13A:
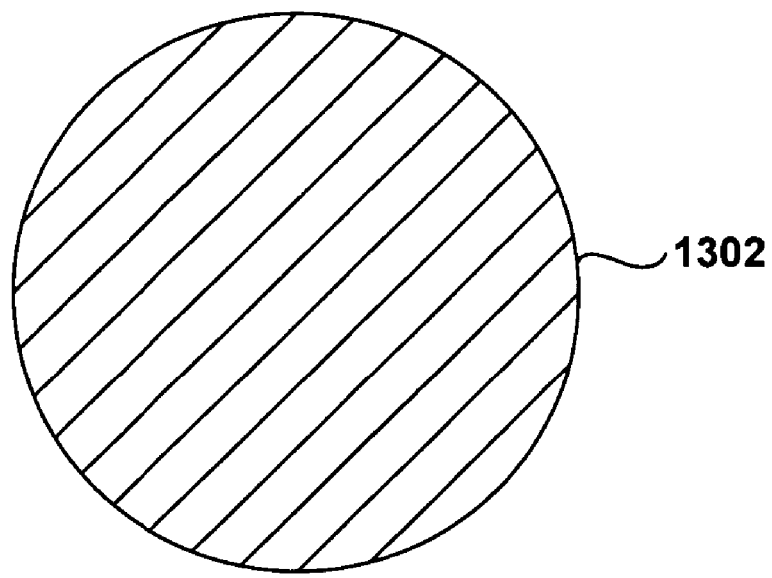
FIGS. 13A-B show with a feature having a uniform intensity distribution and a feature having a non-uniform intensity distribution.
Figure 13B:
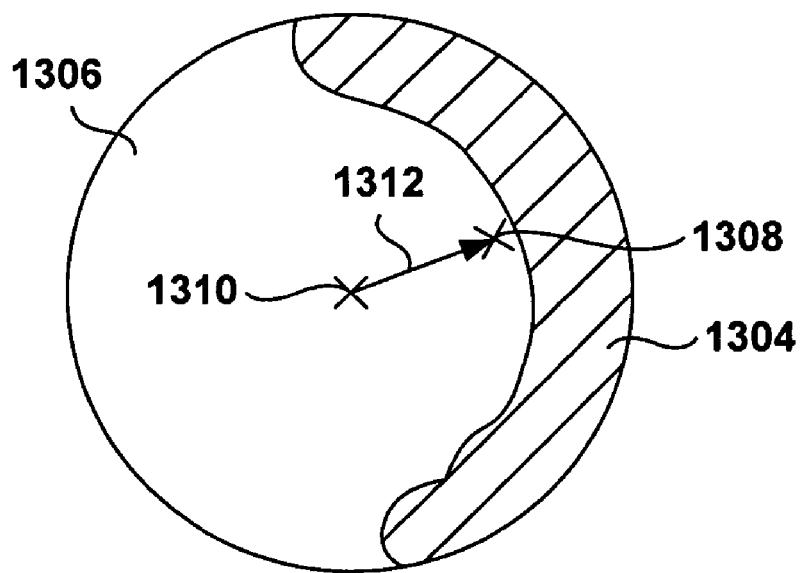

A filter designed to remove from consideration features having non-uniform intensity distributions over the areaa of the features is described in FIGS. 13A-B. FIGS. 13A-B show both a feature having a uniform intensity distribution and a feature having a non-uniform intensity distribution. In FIG. 13A, the disc-shaped area of the image of a feature 1302 is shown with cross-hatching indicating a uniform distribution of moderate intensity values over the entire area of the image of the feature. By contrast, in FIG. 13B, a crescent-shaped portion 1304 of the area of a feature has medium intensity values, while the remaining portion of a feature, 1306, has low intensity values. The signal intensities within the feature shown in FIG. 13B are non-uniformly distributed. Non-uniform distribution of intensities can be detected in a number of different ways. A statistical variance of pixel intensities within the area of the image of a feature can be computed, and features with pixel-intensity variances greater than a threshold variance can be considered to have non-uniform pixel-intensity distributions. For example, the threshold may be a function of biological or electronic noise, or noise on the microarray due to chemical or hybridization processes. Alternatively, as shown in FIG. 13B, a centroid for the pixel intensity distribution 1308 can be computed, and the location of the centroid compared to the location of the geometric center 1310 of the image of the feature. When the distance 1312 between the centroid of pixel-intensity and the geometric center is greater than a threshold distance value, the feature can be considered to have a non-uniform pixel-intensity distribution. Alternatively, both the mean and the median signal statistics can be computed and a feature can be considered to have a non-uniform pixel-intensity distribution if the difference between the mean signal and the median signal exceeds a threshold or if the difference divided by either the mean or the median signal exceeds a threshold. Many other alternative techniques can be employed in order to classify features having uniform and non-uniform pixel-intensity distributions. In step 1106, features having non-uniform pixel distributions are removed from consideration. As noted above, features in certain types of microarrays may not be disc-shaped, and techniques used to compute a metric of uniformity may need to be tailored specifically to the particular feature shapes present in the arrays.

Figure 14:
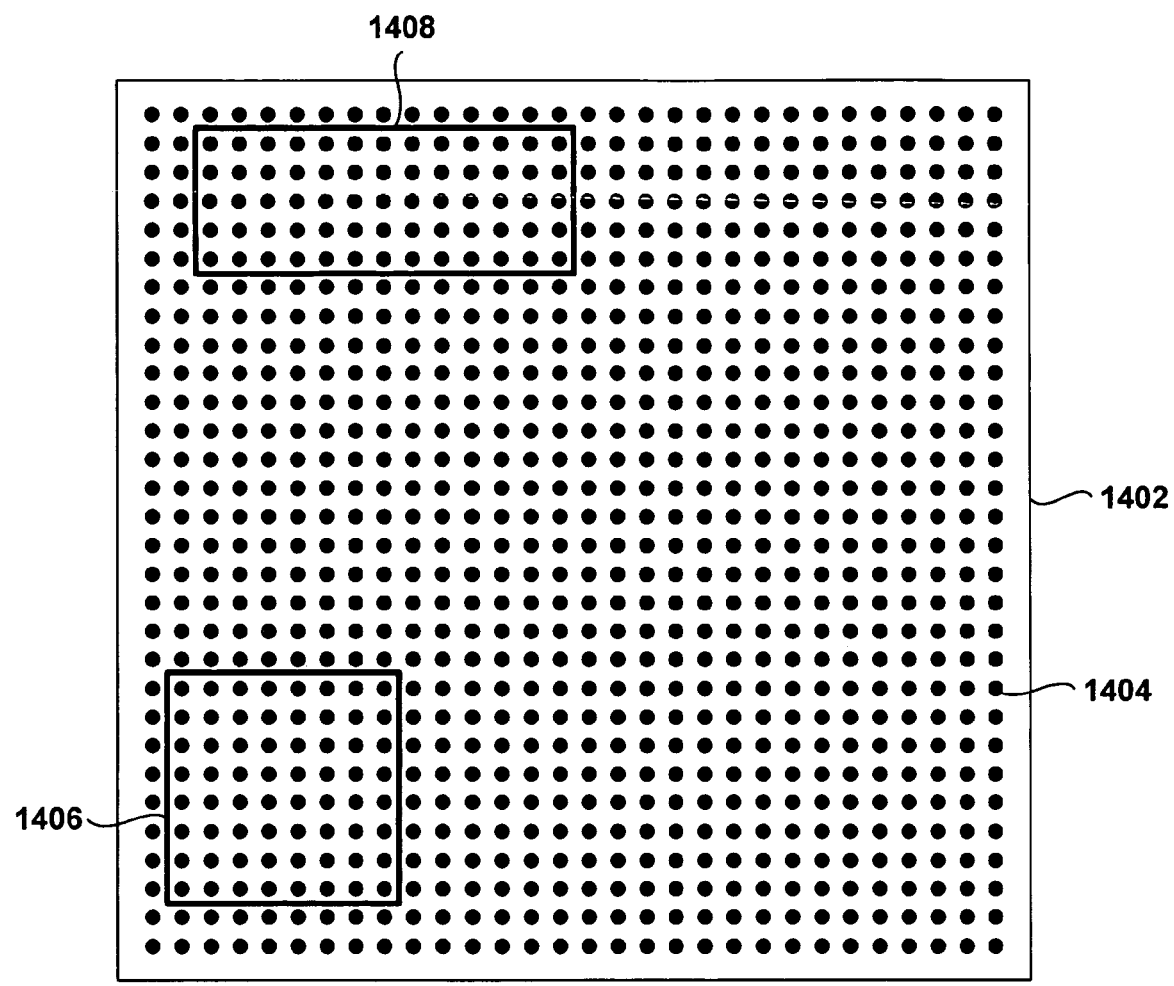
FIG. 14 illustrates two of the many possible sizes and shapes of a moving-window filter.
Figure 15:
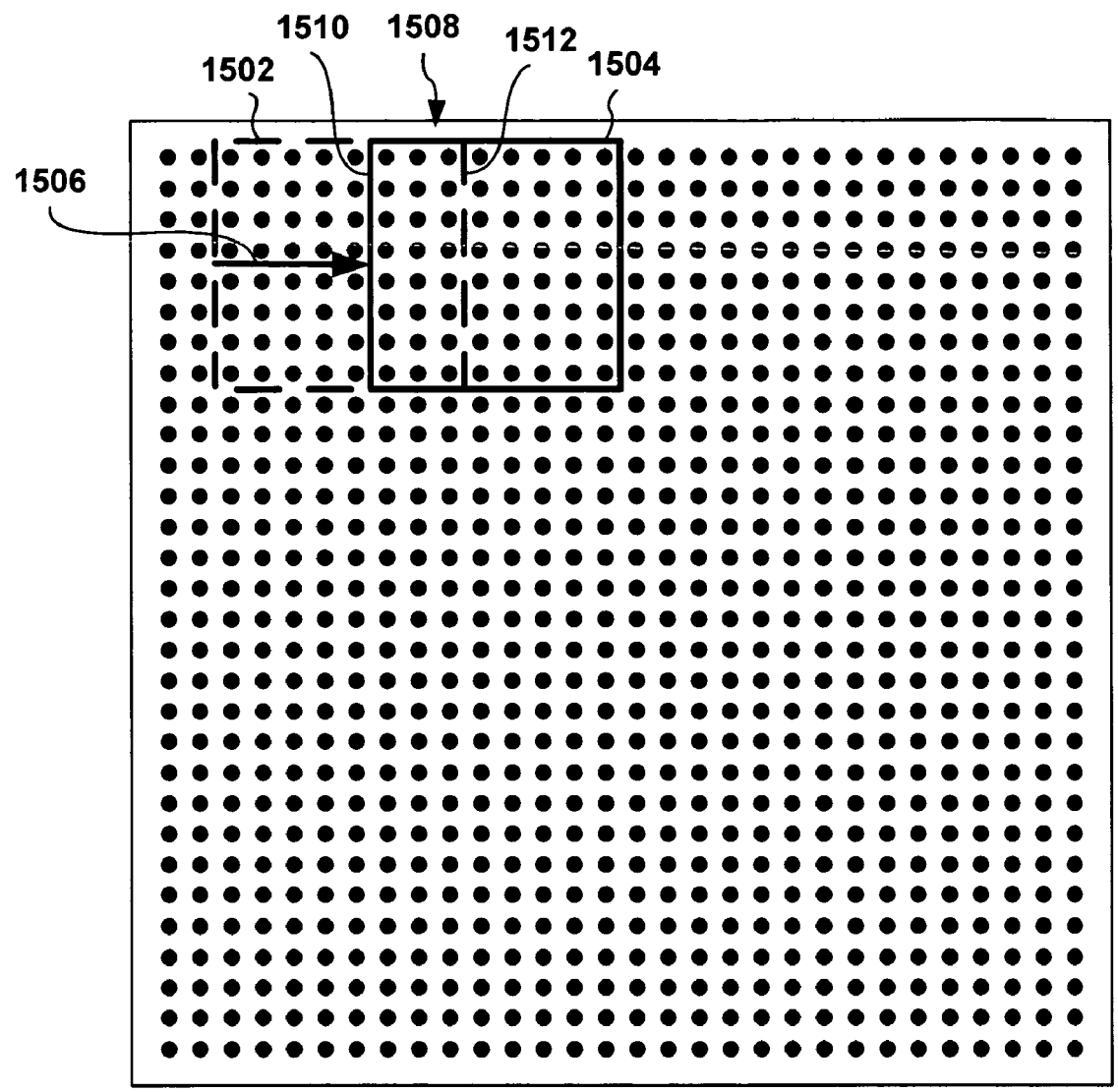
FIG. 15 illustrates incremental movement of a square, moving-window filter.

Next, in optional step 1108, a moving-window filter can be employed to further filter the already filtered microarray data obtained in step 1106. The moving-window filter is employed to select lowest-signal-intensity features of the microarray data. The moving-window filter filtered selects lowest, signal-intensity features from substantially all regions of the microarray. FIGS. 14-16 illustrate the three moving-window-filter, adjustable parameters. The three moving-window-filter, adjustable parameters include: (1) size; (2) increment; and (3) fraction. The size can range from about 1 to about 100 or more features.

FIG. 14 illustrates two of the many possible sizes and shapes of a moving-window filter. In FIG. 14, the disk-shaped features of the microarray 1402, such as feature 1404, are arranged on the surface of the microarray in rows and columns to form a regular two-dimensional matrix, or grid of features. Moving-window filters having square and rectangular boundaries with vertices offset from grid lines are an appropriate choice for use with a grid of microarray features such as microarray 1403, because moving-window-filter boundaries do not intersect with microarray-feature coordinates. For example, in FIG. 14, the boundaries of the square and rectangular moving-window filters 1406 and 1408 do not intersect with features of the microarray 1402.

The moving-window filter is translated, at each step of a moving-window-filter-based filtering process of the already filtered microarray data by translating the window in a selected direction by a fixed number of inter-feature spacings in the selected direction. The increment ranges from about 1 to about 10 or more units in the feature coordinate system. FIG. 15 illustrates incremental translation of a square, 64-feature, moving-window filter. In FIG. 15, a dashed-line boundary 1502 identifies a first moving-window filter position and a solid line boundary identifies a next moving-window filter position to which the moving-window filter is next moved in a single step, during traversal of the data. In FIG. 15, an increment of "5" feature coordinate units in a horizontal direction is employed as indicated by the arrow 1506. Typically, the increment size is less than the length of the sides of the moving-window filter, creating an overlap region. An overlap region 1508 occurs in the example shown in FIG. 15. The overlap region 1508 is located between solid boundary line 1510 and dashed boundary line 1512. In FIG. 15, the moving-window filter is shown moving from left to right. However, the moving-window filter can spatially traverse the microarray feature data in any planar direction. For example, the moving-window filter can be implemented to move from left to right, right to left, vertically upward and downward, or in a diagonal direction.

Figure 16A:
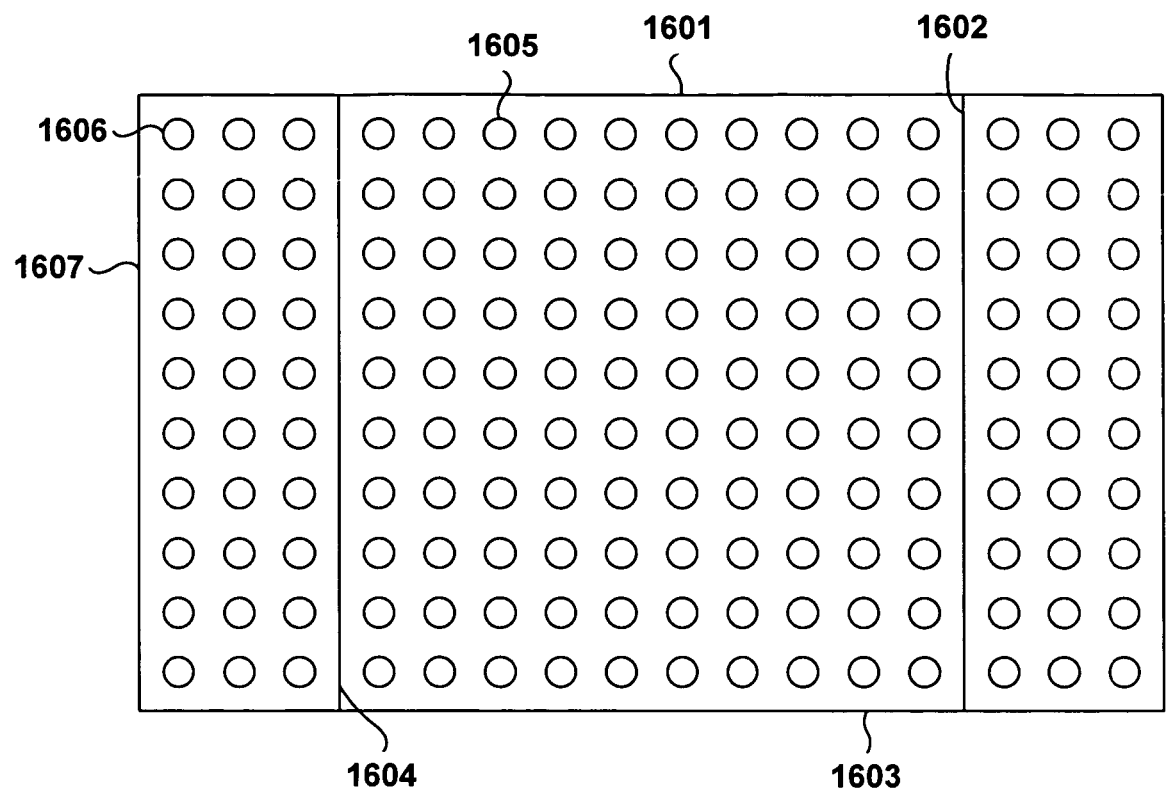
FIG. 16 illustrates a hypothetical selection of lowest-signal-intensity features having coordinates within the boundaries of a moving-window filter.
Figure 16B:
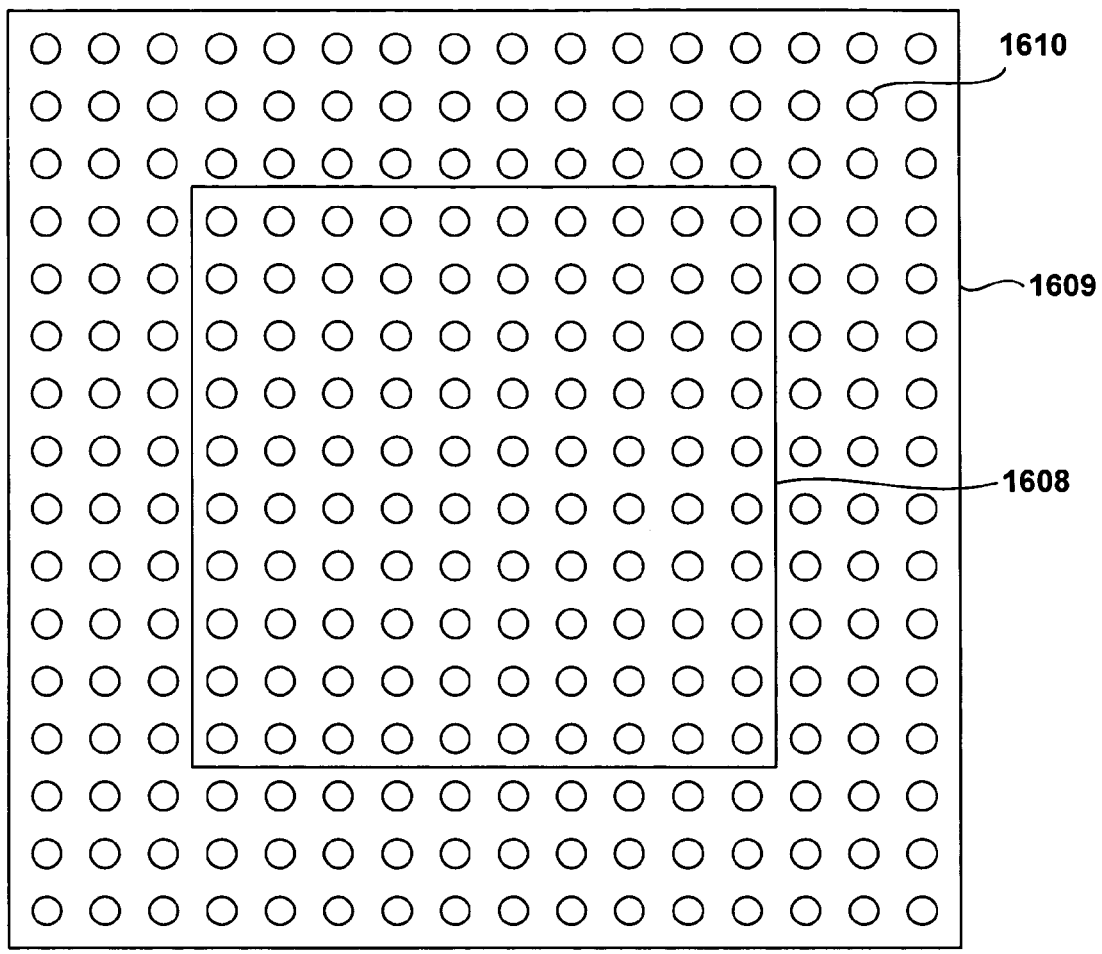

A fraction of lowest, signal-intensity features is selected from each window of the moving-window filter. Note that the moving window filter may also be employed to select highest, signal-intensity features. However, for the sake of illustration, the following discussion is related to selecting lowest, signal-intensity features. For example, assuming that the fraction of lowest-signal-intensity features with respect to all features is $\frac{1}{10}$ then 10 of the lowest, signal-intensity features of a size-100 moving-window filter are selected at each position of the moving-window filter. Note that, typically, 1% of the lowest, signal-intensity features for each window is used. In order to avoid overlooking features near the edge of the microarray boundary during moving-window filtering, the microarray features are extended symmetrically near the boundaries. The size of the symmetric extensions are determined by the size of the moving-window filter. FIG. 16A illustrates one of many possible embodiments for generating symmetric extensions for a hypothetical microarray. In FIG. 16, boundaries 1601-1604 define the outermost boundaries of a hypothetical microarray of features. The features of the hypothetical microarray are identified by open circles, such as open circle 1605. For a square moving-window filter having 9 features, the first three features and the last three features in each row of features are reflected outward from the boundary of the microarray to generate the virtual features comprising symmetric extensions of the microarray. For example, feature 1605 has feature coordinates (1,3), and corresponding reflected-virtual feature 1606 has feature coordinates (1,−3). Both feature 1605 and virtual feature 1606 have identical signal intensities. The moving-window filter traverses the entire set of features and virtual features. The left edge of the moving-window filter starts at the left edge 1607 of the left-hand symmetric extension, traverses the top three rows, and stops when the left edge of the moving-window filter reaches boundary 1602. At each position, the fraction of lowest, signal-intensity features within the boundaries of the moving-window filter are selected. Selected virtual features are stored using the feature coordinates of the original feature. In order to prevent double counting, each selected lowest, signal-intensity feature is checked against the set of already determined lowest, signal-intensity features. Note that, in alternate embodiments, columns of features can be reflected to create symmetric extension along the upper and lower boundaries of the microarray. FIG. 16B illustrates reflecting features in both rows and columns to create a symmetric extension that surrounds the entire set of microarray features. In FIG. 16B, square 1608 identifies the outermost boundary of microarray of features, and square boundary 1609 identifies the outermost boundary of reflected microarray features. The features between square boundary 1608 and square boundary 1609 are the virtual features, such as virtual feature 1610.

Figure 17:
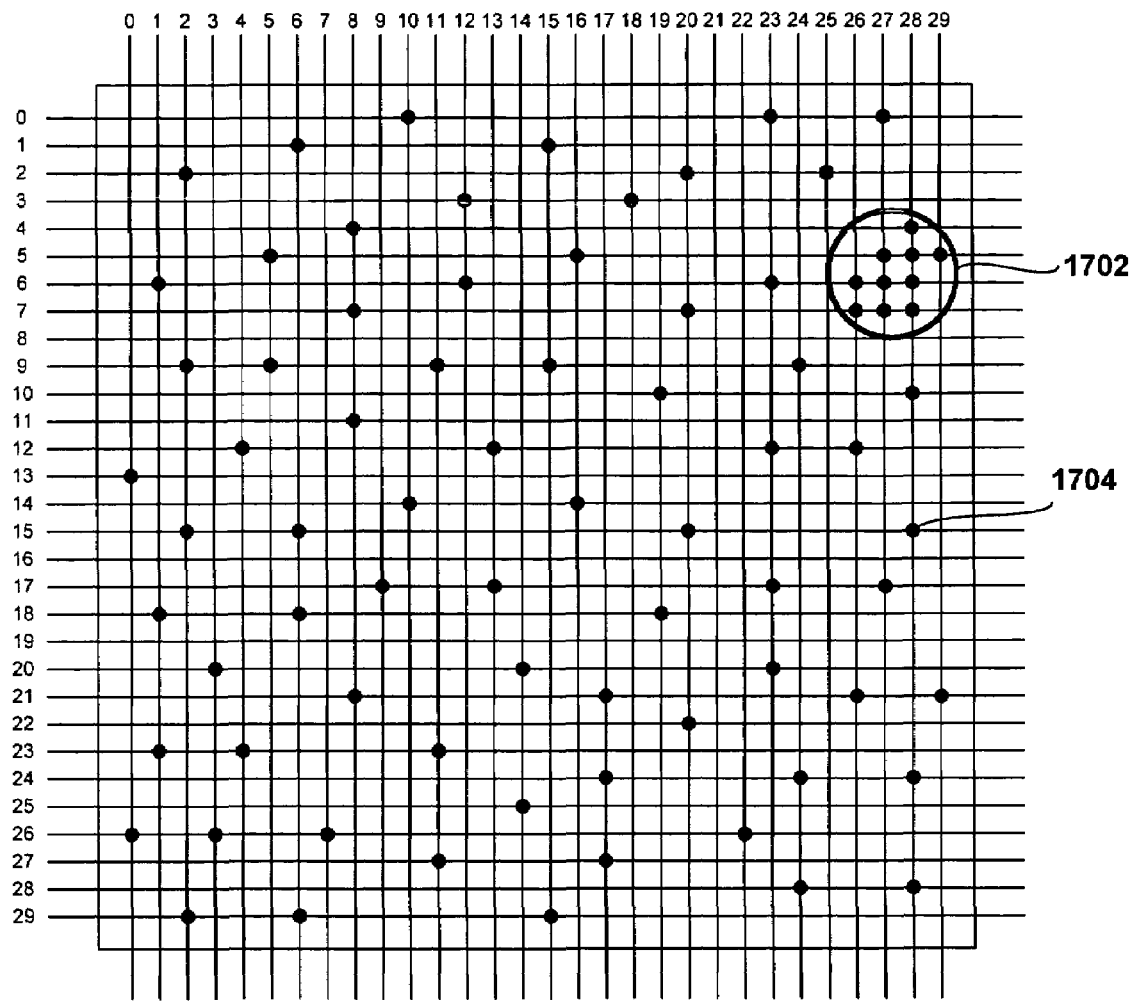
FIG. 17 illustrates a hypothetical display of filtered feature coordinates.

Next, in optional steps 1110, 1112, and 1114, the set of filtered features obtained in step 1106 and optional step 1108 may be examined for clusters of filtered features. Regions where the filtered-feature data are clustered may distort the spatial-intensity-trend quantification described below in steps 1116-1120. If debugging mode is selected by the user in optional step 1110, then, in optional step 1112, the feature coordinates of the filtered feature are displayed. FIG. 17 illustrates a hypothetical display of filtered features coordinates. The display provides the user with an opportunity to visually scan the distribution of filtered features for filtered-feature clusters. For example, in FIG. 17, a cluster of filtered features is located within the boundaries of the circle 1702 in the upper, right-hand corner of the display. Filtered features outside circle 1702, such as filtered feature 1704, appear to be evenly distributed, without clusters. In optional step 1114, if the image reveals regions of clustered filtered features, then the entire filtering process described above, with reference to steps 1102-1108, can be repeated with different parameter values. In optional step 1114, if the image reveals an even distribution of filtered features, then the user can direct the process to step 1116. In alternate embodiments, rather than repeating steps 1102-1108, the user can specify the feature coordinates of clustered filtered features to be filtered from microarray data set. For example, in an alternative embodiment, the user can specify the removal of a number of the filtered features composing the cluster within circle 1702.

The entire set of N filtered features determined in steps 1102-1114 is denoted by $\{(x_i,y_i),I_i,C\}_{i=1}^{N}$, where $(x_i,y_i)$ specifies the feature coordinates of filtered feature i, $I_i$ represents the corresponding intensity of filtered feature i, and C is the channel index. A set of filtered features $\{(x_i,y_i),I_i,C\}_{i=1}^{N}$ can be used to determine a set of data points, referred to as the "best-fit surface" and denoted by S, that characterises the spatial-intensity trends for all feature in the channel C of microarray data set. The set of data points S is constructed by first fitting a best-fit plane, denoted by O, for all features. The general equation for a plane is given by:

$$O(x,y) = p_1 x + p_2 y + p_3 \quad \text{Equation (1)}$$

where $p_1$, $p_2$ and $p_3$ are coefficients determined for each feature coordinate (x, y). The inner for-loop comprising steps 1116, 1118, and 1120, employs a locally-weighted, least-squares method, referred to as "Loess," to determine the coefficients $p_1$, $p_2$, $p_3$ of the best-fit plane O(x, y) for each feature. The Loess method code implemented in the present invention can be obtained from the website http://www.netlib.org/a/dLoess. A written description of the Loess method can be obtained from the website http//www.itl.nist.gov/div898/handbook/pmd/section1/pmd144.htm. (Cleveland, W. S. (1979) "Robust Locally Weighted Regression and Smoothing Scatterplots," *Journal of the American Statistical Association*, Vol. 74, pp. 829-836, and Cleveland, W. S., and Devlin, S. J. (1988) "Locally Weighted Regression: An Approach to Regression Analysis by Local Fitting," *Journal of the American Statistical Association*, Vol. 83, pp. 596-610.)

The following discussion provides a general mathematical description of the Loess method with accompanying figures. For each feature, the constants $p_1$, $p_2$, and $p_3$ are determined by minimizing the locally-weighted, least-squares error given by:

$$\text{Equation (2): } E(p_1, p_2, p_3) = \sum_{i=1}^{M} w_i (O_i - I_i)^2$$

where $O_i = O(x_i, y_i)$;
$w_i$ = the weighting function;
M = total number of neighboring filtered features; and
M<N.

In general, for each feature, the Loess method utilizes a set of M nearest neighbor filtered features to fit a best-fit plane O(x, y). The number of neighboring filtered features associated with each feature is given by:

$$M = ceil(qN)$$

$$\text{where } \frac{p+1}{N} \leq q < 1;$$

p = the degree of the best-fit function; and
q = a user specified input referred to as the "neighborhood size."

Figure 18:
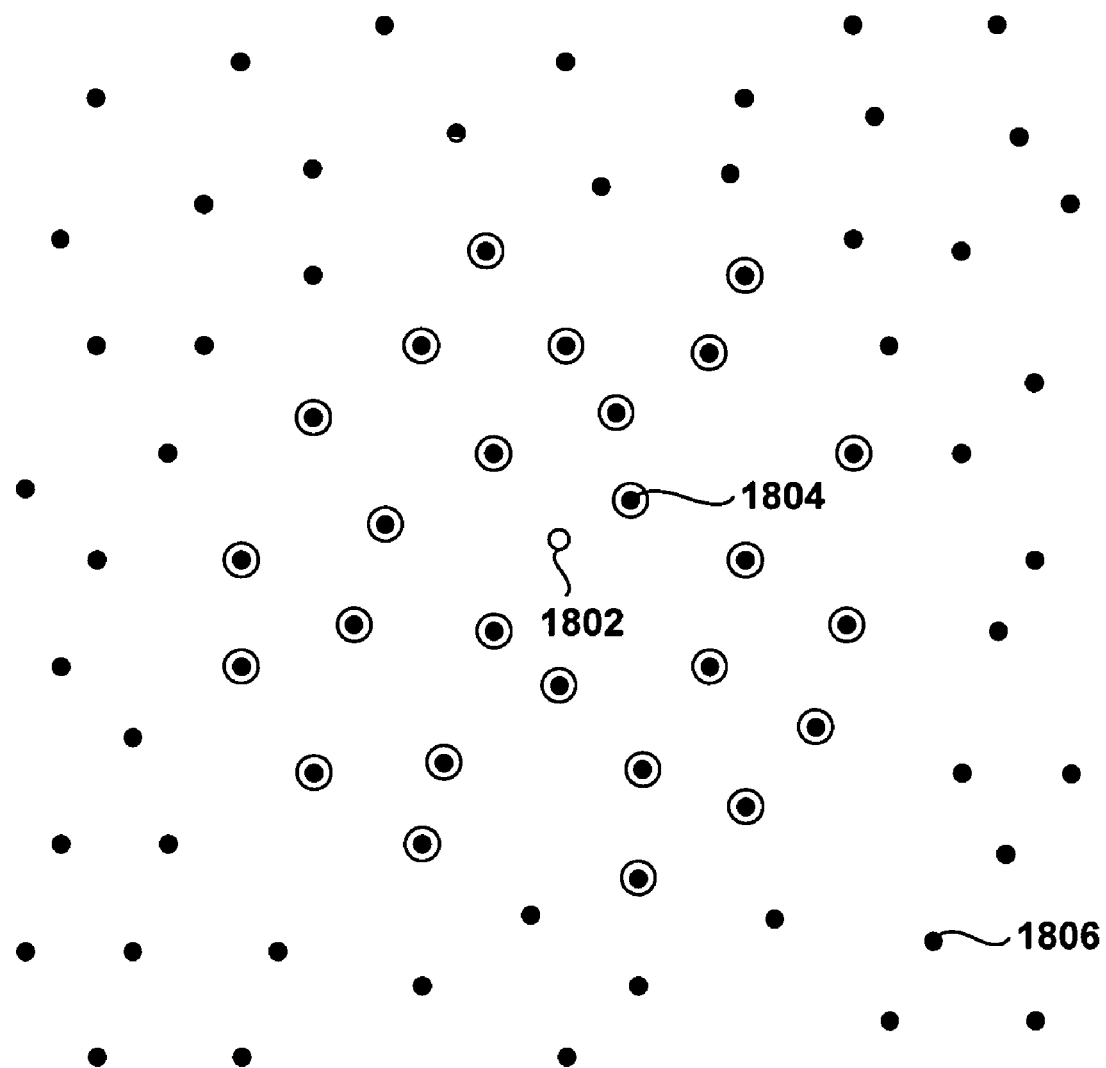
FIG. 18 illustrates a hypothetical set of neighboring filtered features.

Note that, for the best-fit plane O(x, y) given by equation (1), p is equal to "1." Typically, the neighborhood size q is selected somewhere in the range from about 0.20 to about 0.5 and represents the fraction of the total number of filtered features used to determine the best-fit plane O(x, y). FIG. 18 illustrates a hypothetical set of nearest-neighbor-filtered features associated with currently considered feature 1802. In FIG. 18, the set of nearest neighbor filtered features are identified by circled filtered features, such as circled filtered feature 1804. Each filtered feature is assigned a weight according to its distance from the currently considered feature 1802. For example, in FIG. 18, the circled filtered features are assigned a weight $w_i$ according to their distances from currently considered feature 1802, and non-neighboring filtered features, such as filtered feature 1806, are assigned a weight of "0."

One of many possible weighting functions $w_i$ used for the Loess method is the "tricube" function given by:

$$\text{Equation (3): } w_i = w(u_i) = \begin{cases} (1 - u_i^3)^3 & \text{for } 0 \leq u_i < 1 \\ 0 & \text{for } u_i > 1 \end{cases}$$

$$\text{where } u_i = \frac{\rho(x_i, y_i, x, y)}{d(x, y)}$$

is the normalized distance;

$\rho(x_i, y_i, x, y) = \sqrt{(x_i-x)^2 + (y_i-y)^2}$ is the distance from the feature to a neighboring filtered feature;

$d(x,y) = \sqrt{(x-x_m)^2 + (y-y_m)^2}$ the distance from the feature to the farthest, neighboring filtered feature; and $(x_m, y_m)$ is the farthest, neighboring filtered feature.

Figure 19A:
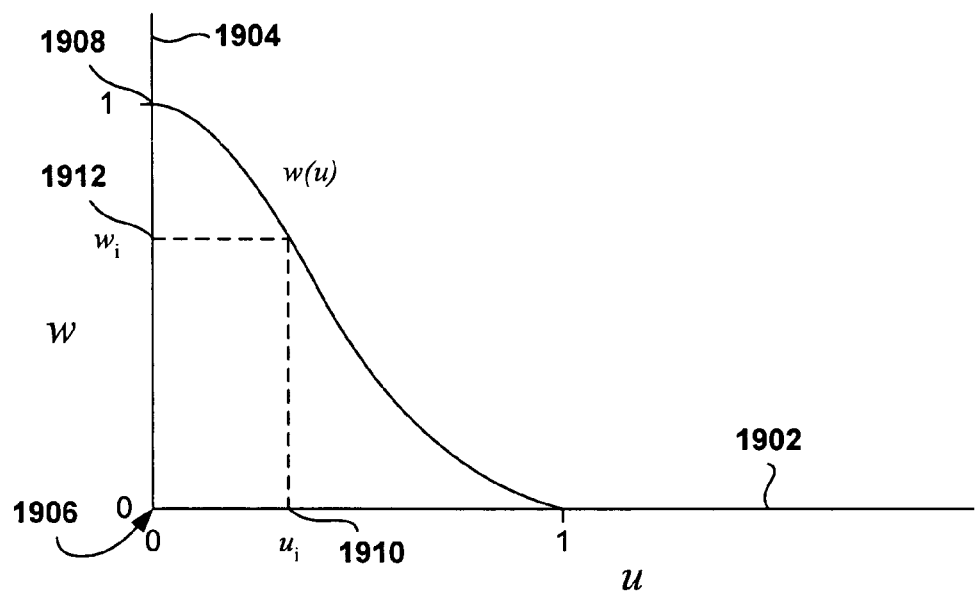
FIGS. 19A-B illustrate a tri-cube weighting function w.
Figure 19B:
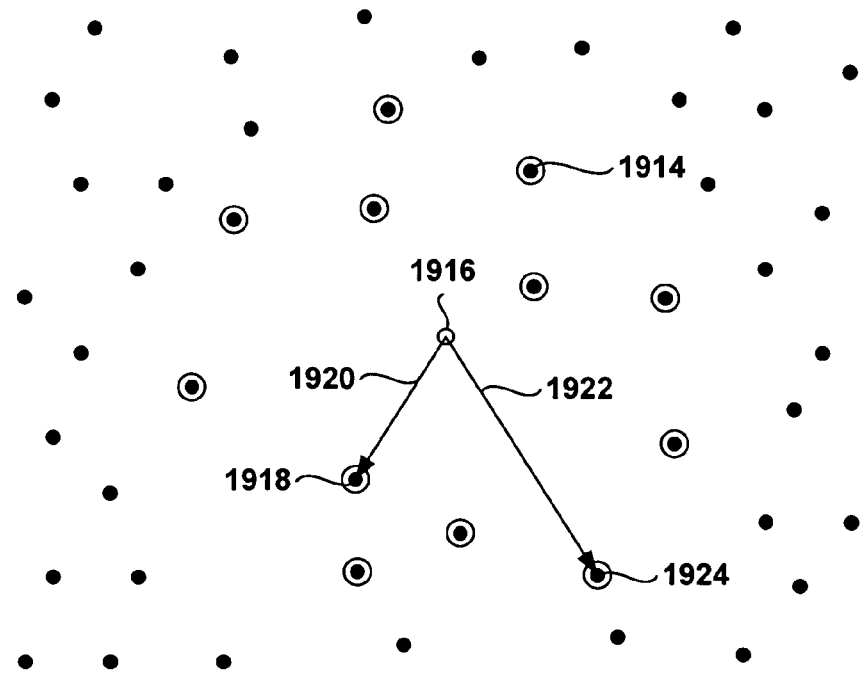

FIGS. 19A-B illustrate the tricube weighting function w. In FIG. 19A, the tricube weighting function is plotted with respect to the horizontal axis 1902, corresponding to the normalized distance $u_i$, and the vertical axis 1904, corresponding to the weighting function values w ranging from "0" 1906 to "1" 1908. For example, a neighboring filtered feature having a normalized distance $u_i$ from the feature is assigned the weight value $w_i$ 1912. Neighboring filtered features are assigned a distance-dependent weight because filtered features that are closer to the feature are assumed to more closely approximate the feature intensity behavior at the feature rather than neighboring filtered features that are farther away.

FIG. 19B illustrates determination of the normalized distance $u_i$ given in equation (3). In FIG. 19B, the neighboring filtered features are identified by circled filtered features, such as circled filtered feature 1914. The normalized distance $u_i$ (1910 in FIG. 19A) from the considered feature 1916 to the neighboring filtered feature 1918 is determined by calculating the distance $\rho(x_i, y_i, x, y)$ 1920 from the considered feature 1916 to the neighboring filtered feature 1918 divided by the distance d(x,y) 1922 from the feature 1916 to the farthest neighboring filtered feature 1924.

The minimum of equation (2) occurs when the gradient of $E(p_1,p_2,p_3)$ equals the zero vector, and is determined as follows:

$$\nabla E(p_1, p_2, p_3) = 2\sum_{i=1}^{M} w_i(O_i - I_i)\nabla O_i = (0, 0, 0)$$

Therefore, the problem of determining the constants $p_1$, $p_2$, and $p_3$ for each feature is reduced to solving a linear system of three equations, each with three unknown constants $p_1$, $p_2$, and $p_3$.

Next, in step 1120, if there are more features, then controls returns to step 1118. In step 1120, if there are no more features for computing the best-fit function, then, in step 1122, the best-fit surface S can be smoothed by repeatedly applying the locally-weighted, least-squares regression for each feature. Rather than using the intensities $I_i$ at the filtered features, the best-fit plane values $O_i$ are used, and the weight function is modified. The locally-weighted, least-squares error is given by:

$$\text{Equation (4): } E(p_1', p_2', p_3') = \sum_{i=1}^{M} W_i(O_i' - O_i)^2$$

where $O_i'=O'(x_i,y_i)=p_1'x_i+p_2'y_i+p_3'$ is the new best-fit plane; and $W_i = w_i \cdot g_i$.

Figure 20:
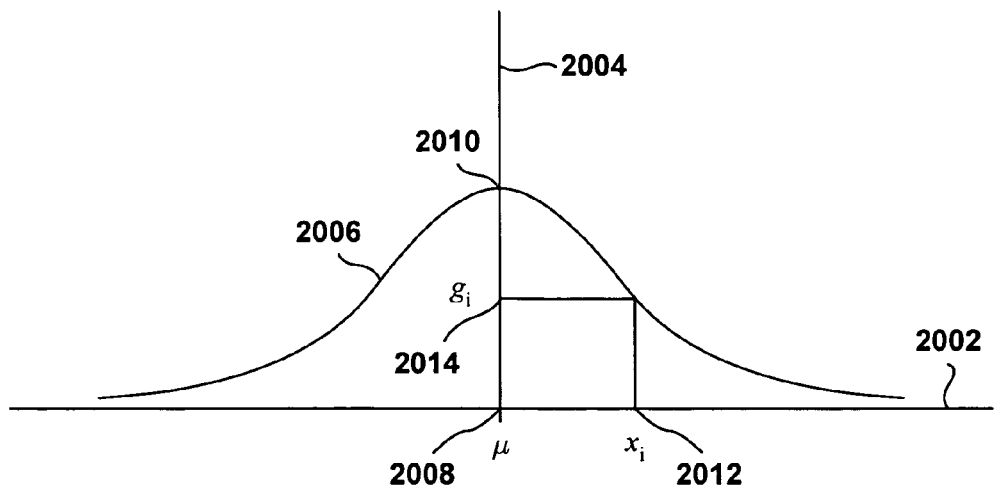
FIG. 20 illustrates a Gaussian weight distribution.

The updated weight function Wi is the product of the tricube weight function $w_i$ from equation (3) and a symmetric distribution function $g_i$. One of many possible symmetric distribution $g_i$ used to reduce the weight for filtered features is given by the Gaussian distribution:

$$\text{Equation (5): } g_i = g(x_i) = \frac{1}{\sigma\sqrt{2\pi}} \exp\left(-\frac{1}{2}\left(\frac{x_i - \mu}{\sigma}\right)^2\right)$$

where $\mu$ and $\sigma$ are the mean and standard deviation, respectively, for the neighborhood of M filtered features i, and $x_i$ is the residual $(I_i-\mu)$. FIG. 20 illustrates a Gaussian weight distribution employed to account for large residuals. In FIG. 20, the horizontal axis 2002 corresponds to the intensity, the vertical axis 2004 corresponds to the normalized weighting function g, and the Gaussian distribution given in equation (5) is represented by the curve 2006. The Gaussian weighting values $g_i$ range from "0" 2008 to "1" 2010. A neighborhood filtered feature having a residual $x_i$ 2012 is assigned the weight value $g_i$ 2014.

Figure 21:
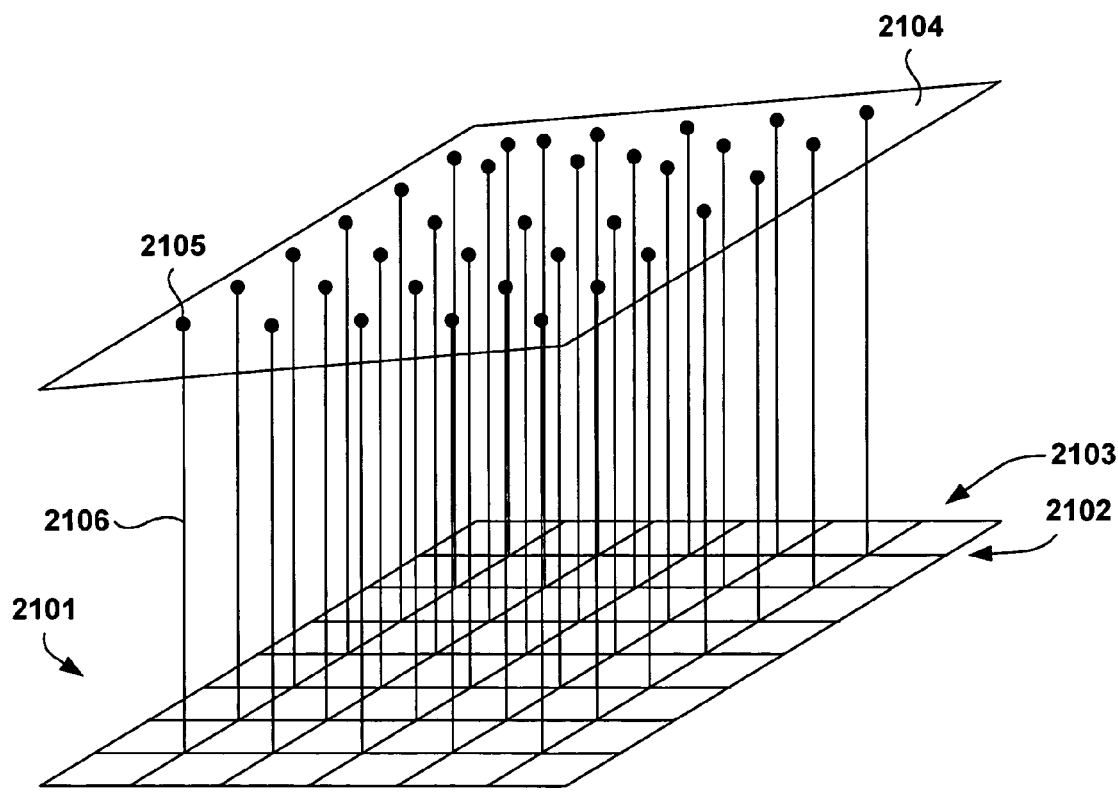
FIG. 21 illustrates a hypothetical set of best-fit surface data points.

After the entire set of L best-fit function intensity values $O_i$, are smoothed, the best-fit surface S is constructed by assembling the best-fit function intensity values $O_i$ to give the following:

$S=\{(x_i,y_i),O_i,C\}_{i=1}^{L}$ \hspace{1cm} Equation (6):

The data points of a best-fit surface S characterizes the spatial-intensity trends for a channel of the microarray data set. FIG. 21 illustrates a surface representing a hypothetical best-fit surface set of data points S. In FIG. 21, the intersections of horizontal and vertical grid lines of the microarray 2101, such as horizontal and vertical grid lines 2102 and 2103, respectively, correspond to feature coordinates. For simplicity of illustration, the best-fit surface S characterizes a plane 2104 that passes through 35 hypothetical best-fit surface data points $O_i$, such as data point 2105. The best-fit intensity values $O_i$ are represented by the height of the vertical lines rising above of the microarray surface, such as vertical line 2106 associated with data point 2105.

Figure 22A:
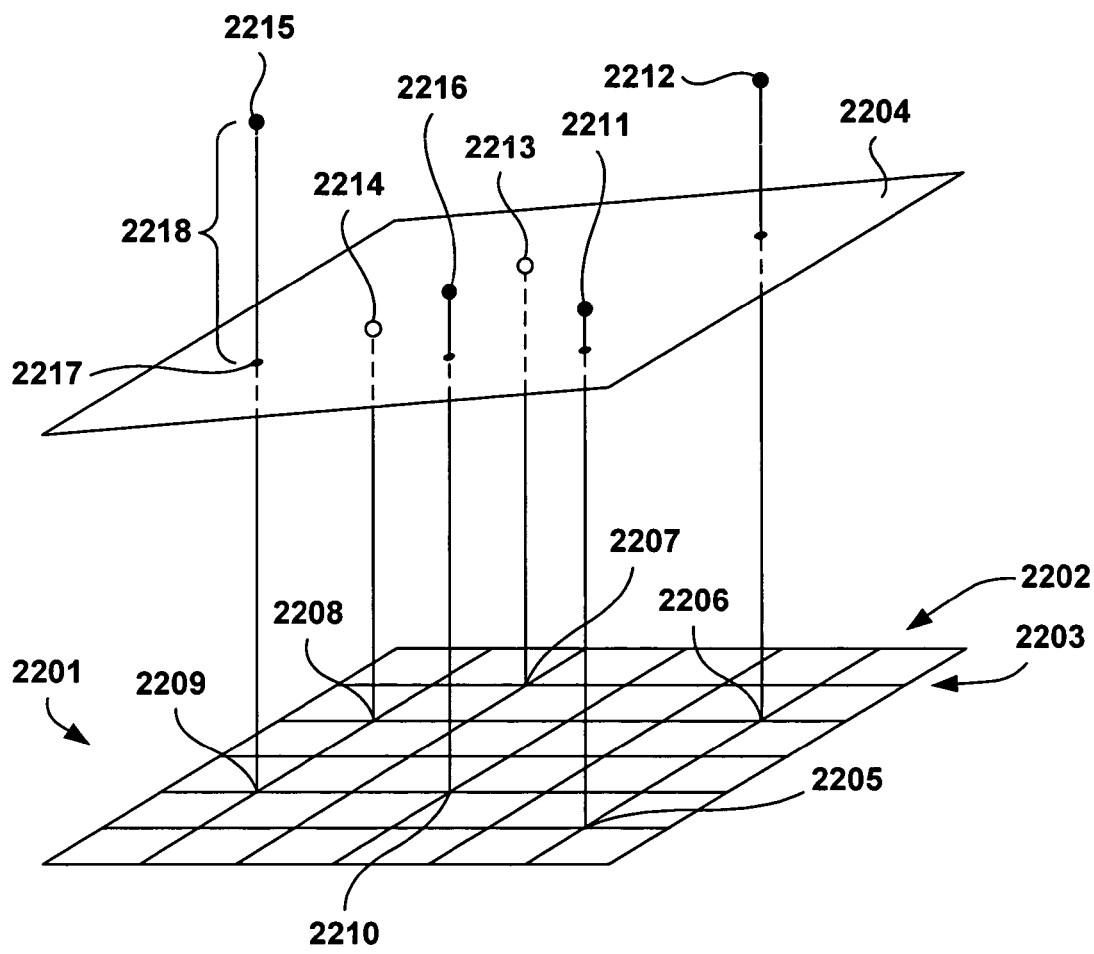
FIGS. 22A-C illustrate three of five possible metrics employed to quantify a spatial-intensity trend.
Figure 22B:
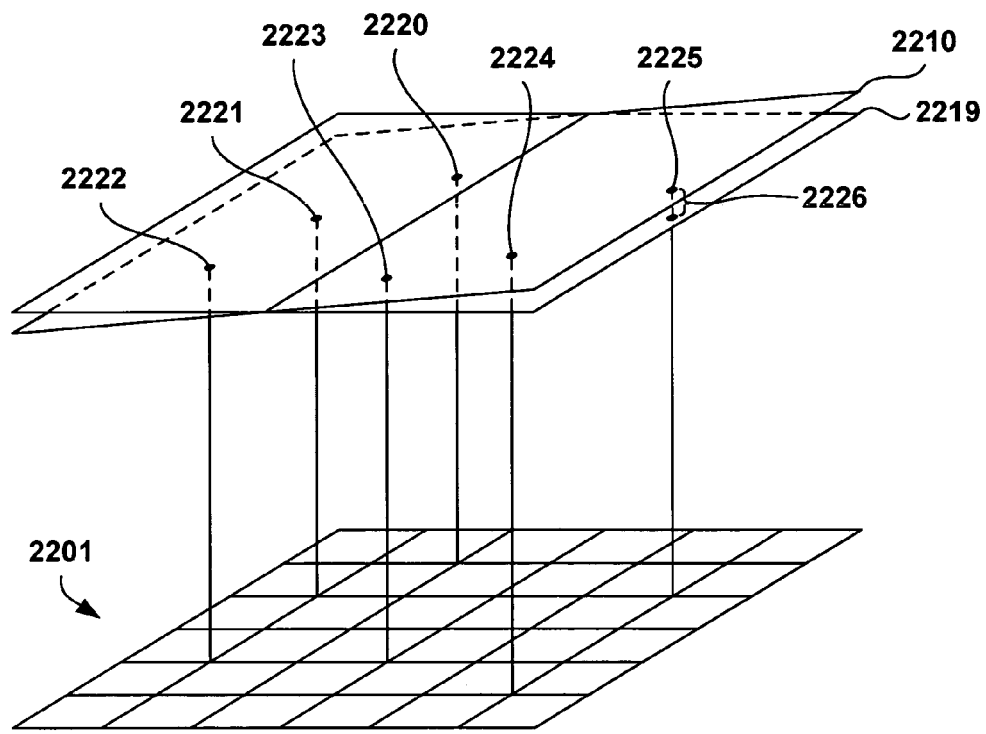
Figure 22C:
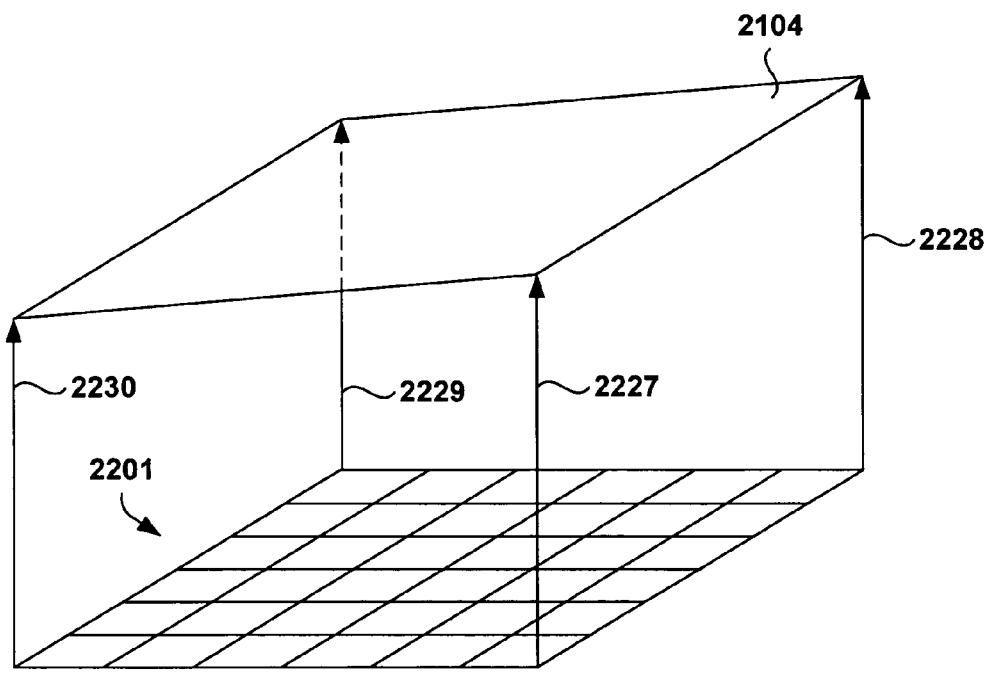

In step 1124, one or more metrics are employed to quantify the spatial intensity trend present in the set of N filtered features. The metrics employed to quantify the spatial-intensity trend include: (1) a root-mean-square ("RMS") difference between N filtered feature intensities $I_i$ and the corresponding values $O_i$; (2) a standard deviation of the values $O_i$; (3) a normalized area; (4) a spatial volume; and (5) a spatial average intensity. FIGS. 22A-C illustrate three of five possible metrics that can be employed to quantify a microarray spatial-intensity trend. In FIGS. 22A-C, the intersections of horizontal and vertical grid lines of the microarray 2201, such as horizontal and vertical grid lines 2202 and 2203, respectively, correspond to feature coordinates. Surface 2204 represent the surface passing through best-fit data points $O_i$.

The RMS difference between the filtered features $I_i$ and the corresponding best-fit values $O_i$, referred to as the "Spatial RMS Filtered minus Fit," is determined by calculating the following:

$$\text{Equation (7): Spatial RMS Filtered minus Fit} = \sqrt{\frac{\sum_{i=1}^{N}(I_i - O_i)^2}{N}}$$

Equation (7) is a measure of the typical size of the difference between the filtered feature intensities $I_i$ and the corresponding surface intensities $O_i$. In other words, equation (7) is a measure of the residual difference between the lowest-signal-intensity features (or highest-signal-intensity trends) and the surface S. FIG. 22A is a plot of the set of filtered features and the surface 2204. In FIG. 22A, the corresponding intensities $I_i$ of filtered features 2205-2210 are identified by solid and open circles 2211-2216, respectively. Solid circles 2211, 2212, 2214, and 2216 identify those filtered-feature intensities $I_i$ that lie above the surface 2204, and open circles 2213 and 2215 identify those filtered-feature intensities $I_i$ that lie below the surface 2204. The numerator under the radical in equation (7) is the sum of the square of the distance from filtered feature intensities $I_i$ to the corresponding surface value $O_i$. For example, the distance from filtered feature intensity 2215 to the best-fit point $O_i$ 2217 is the distance 2218.

The standard deviation of the set of data points S is referred to as the "Spatial RMS Fit," and is determined by calculating the following:

$$\text{Equation (8): Spatial RMS Fit} = \sqrt{\frac{\sum_{i=1}^{N}(O_i - \overline{O})^2}{N}}$$

where $\overline{O} = \dfrac{\sum_{i=1}^{N} O_i}{N}$ is the mean of the set $\{(x_i, y_i), O_i\}_{i=1}^{N}$ corresponding the filtered features.

Equation (8) provides a measure of the amount of dispersion about the mean $\overline{O}$, assuming that the mean is the center of the filtered features. In other words, the standard deviation reveals how closely the surface values $O_i$ correspond to the $\overline{O}$ mean. FIG. 22B is a plot of the surface 2204 and the mean $\overline{O}$ 2219. Note that the mean $\overline{O}$ 2219 is a constant represented by a plane parallel to the microarray surface. The standard deviation measures the RMS distance from the best-fit values $O_i$, represented by points 2220-2225, and the mean $\overline{O}$ 2219. For example, in FIG. 22B, the distance from the surface value $O_i$ 2225 to the mean $\overline{O}$ 2219 directly below is given by the distance 2226. Values for equation (8) that are close to "0" indicate that the best-fit values $O_i$ are located close to the mean $\overline{\mathbf{0}}$. However, large values for equation (8) imply that the best-fit values $O_i$ are farther from the mean.

The normalized area, referred to as "spatial surface area" is determining by calculating the surface area of surface 2204 divided by the surface area of the microarray 2201. In FIG. 22C, arrows 2227-2230 projected perpendicular to the microarray surface identify the boundaries of the surface 2204. The area of surface 2204 is denoted by A, and the surface area of microarray 2201 is denoted by A'. The spatial surface area is determined by computing $$\frac{A}{A'}.$$

Values of $$\frac{A}{A'}$$

close to "1" suggests that there is little spatial-intensity trend. However, values of $$\frac{A}{A'}$$

larger than "1" suggests the presence of a spatial-intensity trend.

The spatial volume is approximated by computing:

$$\text{Spatial volume} = \frac{V - \text{offset}}{A'}$$

$$\text{where } V = \sum_{i=1}^{L} O_i;$$

offset $= O_{i,min} \cdot L$; and

A'=the surface area of the microarray.

A spatial volume value close to the value "0" suggests little spatial-intensity trend is present. However, a spatial volume value larger than "0" suggests the presence of a spatial-intensity trend.

The spatial average fit of the best-fit intensities is computed according to the following expression:

$$\text{Spatial average fit} = \frac{\sum_{i=1}^{N} O_i}{N}$$

The above described metrics can be used as assess the overall quality of a microarray hybridization assay, and therefore, can be used to discard any microarray data sets that cannot trusted to yield an accurate assessment of gene expression levels in a microarray hybridization assay. For example, a microarray data set having a standard deviation larger than a user defined standard-deviation threshold could be used as a criterion for discarding the entire microarray data set.

Next, in step 1126, the feature intensities for a given channel can be corrected by removing the spatial-intensity trend in order to improve the microarray data quality. As described above, a spatial-intensity trend attributed to the background adds to the signal intensities of those affected features. Therefore, for each feature of the microarray, spatial-intensity trends attributed to the background can be corrected as follows:

$$I_C^{corrected}(x,y) = I_C(x,y) - O_C(x,y)$$

where (x,y)=the feature coordinates;
C=channel index;
$I_C(x,y)$=the feature signal intensity;
$O_C(x,y)$=best-fit surface intensity; and
$I_C^{corrected}(x,y)$=corrected feature signal intensity.

For high-intensity features, spatial-intensity trends are often proportional to the intensity of the signal. For example, a hypothetical feature having a signal intensity of 1,000 is increased to 1,100, while another hypothetical feature on the same microarray having a signal intensity of 10,000 is increased to 11,000. Rather than subtracting this kind of spatial-intensity trend from each feature, the spatial-intensity trend may be corrected by dividing each feature intensity by the corresponding normalized best-fit surface intensity. For example, consider a dome-shaped, spatial-intensity trend having highest signal-intensity features of 1000 in the middle of the microarray and highest signal-intensities features of 500 around the edges of the microarray. The normalized best-fit surface intensities are determined by dividing all best-fit surface intensities by 1000 to give corresponding signal intensities of 1.000 in the middle of the microarray and signal intensities of 0.500 around the edges. The microarray feature intensities are corrected by dividing each feature intensity by the corresponding normalized best-fit surface intensity.

Next, in step 1128, if the multi-channel microarray data has more channels, then steps 106-1126 are repeated. In step 1128, if there are no more channels to quantify the spatial-intensity trend, then return to the calling function.

Figure 23:
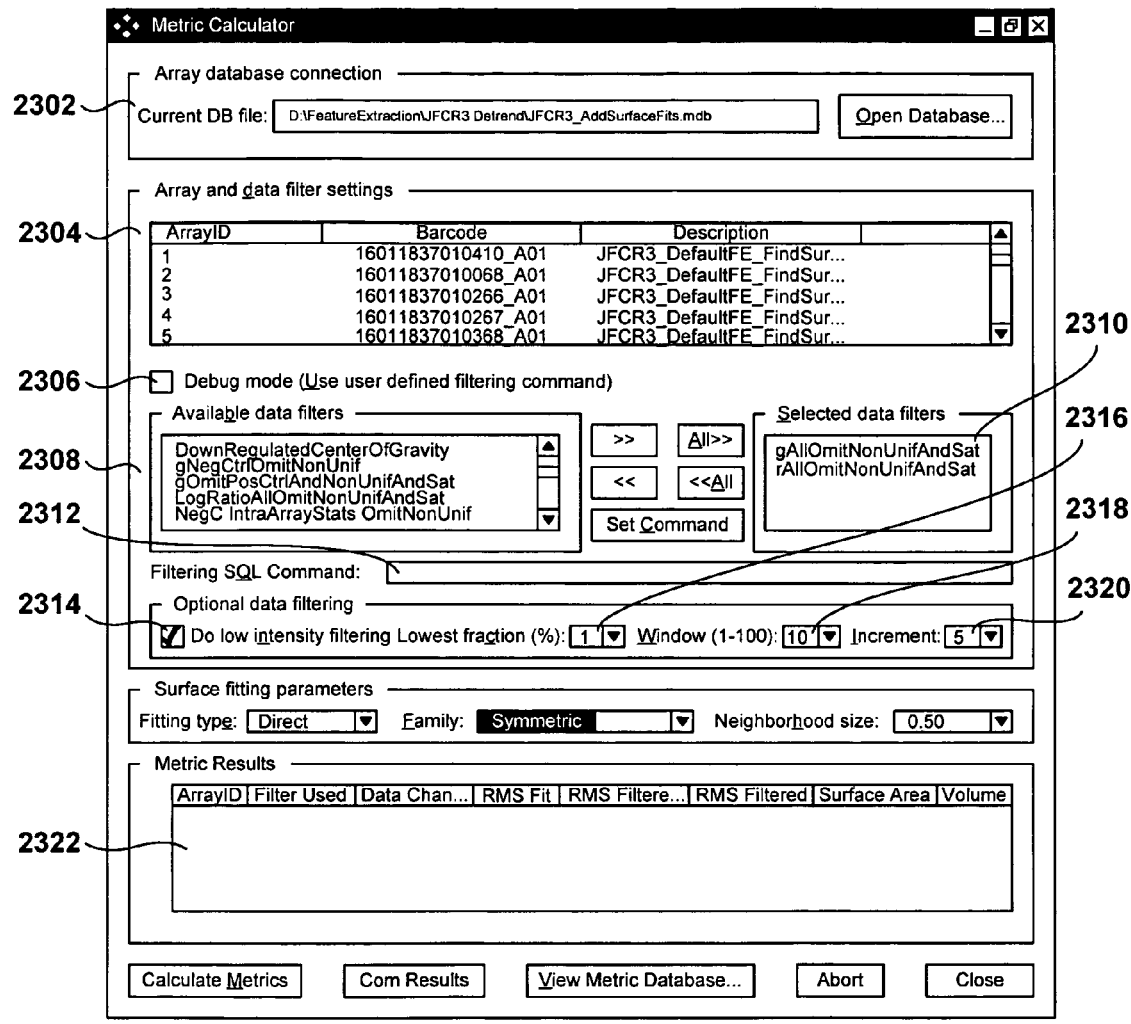
FIG. 23 illustrate one of many possible embodiments for a user interface.

FIG. 23 illustrate one of many possible embodiments for a user interface. In window 2302, a user can load a database of microarray data. In window 2304, each microarray data set stored in the microarray database is listed in a scrollable display window. In selection box 2306, the optional debug mode described above in relation to steps 1110, 1112, and 1114 can be selected. In scrollable window 2308, the available filters described above in relation to step 1106 are displayed. In window 2310, the selected filters listed in scrollable window 2308 are listed in a display. In input window 2312, the optional moving-window filter, described above in relation to step 1108, can be selected. If the optional moving-window filter is selected, then in selection box 2314 low intensity features can be selected for determining the best-fit surface. In selection window 2316, the fraction of features can be selected, as described above in relation to FIG. 16. In input window 2318, the size of the moving-window filter can be entered, as described above in relation to FIG. 14. In selection window 2320, the increment as described above, with reference to FIGS. 15, can be selected. In display window 2322, each microarray data set metrics are displayed.

Although the present invention has been described in terms of a particular embodiment, it is not intended that the invention be limited to this embodiment. Modifications within the spirit of the invention will be apparent to those skilled in the art. For example, an almost limitless number of different implementations of the many possible embodiments of the method of the present invention can be written in any of many different programming languages, embodied in firmware, embodied in hardware circuitry, or embodied in a combination of one or more of the firmware, hardware, or software, for inclusion in microarray data processing equipment employing a computational processing engine to execute software or firmware instructions encoding techniques of the present invention or including logic circuits that embody both a processing engine and instructions. In alternate embodiments, the best-fit function can be a quadratic function given by:

$$O(x,y)=p_1 x^2+p_2 xy+p_3 y^2+p_4 x+p_5 y+p_6$$

where $p_1, p_2, p_3, p_4, p_5$, and $p_6$ are constants determined for each feature.

In alternate embodiments, an interpolating function can be used to approximate the filtered features. Interpolation involves construction of a function that assumes the values $I_i$ at each $(x_i, y_i)$ for each filtered features. In alternate embodiments, the shape of the moving-window filter can be adjusted to accommodate a variety of microarray feature layouts. For example, diamond, hexagonal, triangular, circular, or elliptical or any other closed boundary may be employed. In alternate embodiments, the method of the present invention can be applied to one or more microarray data sets.

The foregoing description, for purposes of explanation, used specific nomenclature to provide a thorough understanding of the invention. However, it will be apparent to one skilled in the art that the specific details are not required in order to practice the invention. The foregoing description of specific embodiments of the present invention are presented for purposes of illustration and description. They are not intended to be exhaustive or to limit the invention to the precise forms disclosed. Obviously many modifications and variations are possible in view of the above teachings. The embodiments are shown and described in order to best explain the of the invention and its practical applications, to thereby enable others skilled in the art to best utilize the invention and various embodiments with various modifications as are suited to the particular use contemplated. It is intended that the scope of the invention be defined by the following claims and their equivalents.

The invention claimed is:

1. A method for quantifying and correcting spatial-intensity trends in a microarray data set having one or more channels, the method comprising:
   selecting a set of features, based on intensity level, from each channel of the microarray data set;
   determining surface intensities for each feature in the channel of the microarray data set from a surface calculated based on intensity levels of the selected set of features;
   quantifying the spatial-intensity trends in each channel of the microarray data set based on the surface intensities; and
   correcting feature intensities for each channel of the multi-channel, microarray data set based on the determined surface intensities; and
   performing at least one of: outputting a result of the method to a display; outputting a result of the method to memory; outputting a result of the method to a computer on a network; or outputting a result to a human user in human-readable format.

2. The method of claim 1 wherein selecting the set of features further includes selecting lowest-signal-intensity features or highest-signal-intensity features.

3. The method of claim 1 wherein the selected features are negative-control features or positive-control features.

4. The method of claim 2 wherein said selecting lowest, signal-intensity features, or highest-signal-intensity features further includes employing an optional window filter.

5. The method of claim 4 wherein employing the optional moving-window filter further comprises:
   varying the moving-window filter size;
   incrementally moving the moving-window filter; and
   selecting a fraction of the lowest-signal-intensity features or the highest-signal intensity features that are within the boundaries of the moving-window filter.

6. The method of claim 5 wherein employing an optional moving-window filter further includes symmetrically extending boundary features of the microarray data set.

7. The method of claim 1 wherein selecting the set of features further includes excluding features having non-uniform intensity distributions.

8. The method of claim 1 wherein determining the surface for each feature further includes using locally-weighted, least-squares regression.

9. The method of claim 8 wherein using locally-weighted, least-squares regression further includes determining a user-defined neighborhood of filtered features associated with each feature.

10. The method of claim 9 wherein each neighborhood within the set of features is substantially the same size.

11. The method of claim 1 wherein selecting the set of features further includes employing a visual display to select non-clustering features.

12. The method of claim 1 wherein measuring the spatial-intensity trend in each channel of the multi-channel, microarray data set further includes determining, for each surface, one or more of:
   a spatial root mean square filtered feature minus fit;
   a spatial root mean square fit;
   a normalized area;
   a spatial volume;
   a mean of the selected feature signal intensities; and
   a root mean square of the selected feature signal intensities.

13. The method of claim 1 wherein said correcting feature intensities includes subtracting from each feature intensity a corresponding surface intensity.

14. The method of claim 1 wherein correcting feature intensities for each channel of the data set further includes:
   normalizing the surface to the highest intensity value; and
   dividing each feature intensity of the data set by the corresponding normalized surface intensity.

15. The method of claim 1 wherein quantifying and correcting spatial-intensity trends further includes quantifying and correcting spatial-intensity trends in algebraically transformed features intensities.

16. The method of claim 1, further comprising performing at least one of:
- storing a spatial-intensity trend data set, produced by the method of claim 1, in a computer readable medium; and
- transferring the spatial intensity trend data set to an intercommunicating entity via electronic signals.

17. The method of claim 1, further comprising storing results produced by the method of claim 1 in a computer-readable medium.

18. A method comprising communicating to a remote location a spatial-intensity trend obtained by a method of claim 1.

19. A method comprising receiving data produced by using the method of claim 1.

20. A physical computer readable medium carrying software to execute the method of claim 1.

21. A program on physical computer readable media configured to, when executed, provide a computer user interface comprising:
- a listing of each microarray data set stored in a microarray database;
- an optional debug mode;
- a scrollable display listing available filters;
- a selection window for selecting optional moving-window filtering;
- an input window for inputting a size of the optional moving-window filter;
- an input window for selecting a fraction of selected filtered features;
- an input window for selecting an increment of the moving window filter; and
- a display window for displaying metric values for each microarray data set that allows a user to determine which surfaces are added to the database.

22. A system for determining spatial intensity trends in microarrays data, the system comprising:
- a computer processor;
- a communications medium by which one or more microarray data sets are received by the microarray-data processing system;
- a program, stored in the one or more memory components and executed by the computer processor to perform a method that selects a set of features, based on intensity levels, from each channel of the microarray data set; determines surface intensities for each feature in the channel of the microarray data set based on the selected set of features; quantifies the spatial-intensity trends in each channel of the microarray data set based on the surface intensities; corrects feature intensities for each channel of the multi-channel, microarray data set based on the determined surface intensities; and performs at least one of: outputting a result of the method to a display; outputting a result of the method to memory; outputting a result of the method to a computer on a network; or outputting a result to a human user in human-readable format.

* * * * *